(12) United States Patent
Gall et al.

(10) Patent No.: US 8,118,952 B2
(45) Date of Patent: Feb. 21, 2012

(54) OSTEOSYNTHETIC IMPLANTS AND METHODS OF USE AND MANUFACTURE

(75) Inventors: Kenneth A. Gall, Atlanta, GA (US);
Jeffrey A. Tyber, Bethlehem, PA (US);
Douglas Pacaccio, Glenview, IL (US)

(73) Assignee: Medshape Solutions, Inc., Atlanta, GA (US)

( * ) Notice: Subject to any disclaimer, the term of this patent is extended or adjusted under 35 U.S.C. 154(b) by 910 days.

(21) Appl. No.: 11/659,770

(22) PCT Filed: Apr. 21, 2006

(86) PCT No.: PCT/US2006/015207
§ 371 (c)(1),
(2), (4) Date: May 8, 2008

(87) PCT Pub. No.: WO2006/116164
PCT Pub. Date: Nov. 2, 2006

(65) Prior Publication Data
US 2008/0269808 A1    Oct. 30, 2008

Related U.S. Application Data

(63) Continuation-in-part of application No. 11/112,865, filed on Apr. 21, 2005, now Pat. No. 7,985,222.

(60) Provisional application No. 60/563,952, filed on Apr. 21, 2004.

(51) Int. Cl.
*C22F 1/10* (2006.01)
*A61F 2/28* (2006.01)

(52) U.S. Cl. ........................ 148/563; 606/60; 623/23.53

(58) Field of Classification Search .................. None
See application file for complete search history.

(56) References Cited

U.S. PATENT DOCUMENTS

| | | | |
|---|---|---|---|
| 4,452,236 A | 6/1984 | Utsugi | 128/4 |
| 4,665,906 A | 5/1987 | Jervis | |
| 5,067,957 A | 11/1991 | Jervis | |
| 5,120,175 A | 6/1992 | Arbegast et al. | 411/501 |
| 5,190,546 A | 3/1993 | Jervis | |
| 5,265,456 A | 11/1993 | Kennedy et al. | 72/342.7 |
| 5,415,660 A | 5/1995 | Campbell et al. | |
| 5,486,183 A | 1/1996 | Middleman et al. | |

(Continued)

FOREIGN PATENT DOCUMENTS

CN        2472682 Y        1/2002

(Continued)

OTHER PUBLICATIONS

English Translation of WO 2006/120355 (listed above).

(Continued)

*Primary Examiner* — George Wyszomierski
(74) *Attorney, Agent, or Firm* — Greenberg Traurig, LLP

(57) ABSTRACT

Bone fracture fixation devices, systems and methods of use and manufacture are provided. One such bone fixation device includes an elongate element having a responsive zone. The element is adapted to be coupled to the bone so that the responsive zone is positioned adjacent a fracture or fusion site in the bone. The responsive zone is adapted to apply a desired pressure to the bone when coupled thereto. In some embodiments, the responsive zone comprises a shape memory material, which may be nickel titanium or Nitinol, to apply compressive pressure across the fracture or fusion site for longer periods of time than standard bone screws.

29 Claims, 17 Drawing Sheets

THE STRESS-STRAIN DIAGRAM FOR LIVING TISSUES AND A NiTi ALLOY [I].

U.S. PATENT DOCUMENTS

| | | | |
|---|---|---|---|
| 5,505,734 A | 4/1996 | Caniggia et al. | 606/63 |
| 5,597,378 A | 1/1997 | Jervis | |
| 5,601,572 A | 2/1997 | Middleman et al. | |
| 5,632,746 A | 5/1997 | Middleman et al. | |
| 5,720,754 A | 2/1998 | Middleman et al. | |
| 5,749,879 A | 5/1998 | Middleman et al. | |
| 5,820,628 A | 10/1998 | Middleman et al. | |
| 5,836,066 A * | 11/1998 | Ingram | 29/90.7 |
| 5,882,444 A | 3/1999 | Flomenblit et al. | |
| 5,904,690 A | 5/1999 | Middleman et al. | |
| 5,964,770 A | 10/1999 | Flomenblit et al. | |
| 6,004,330 A | 12/1999 | Middleman et al. | |
| 6,306,141 B1 | 10/2001 | Jervis | |
| 6,447,523 B1 | 9/2002 | Middleman et al. | |
| 6,451,025 B1 | 9/2002 | Jervis | |
| 6,533,805 B1 | 3/2003 | Jervis | |
| 6,637,995 B1 | 10/2003 | White | 411/339 |
| 6,688,828 B1 | 2/2004 | Post | 411/383 |
| 6,986,774 B2 | 1/2006 | Middleman et al. | |
| 7,005,018 B2 * | 2/2006 | Julien | 148/563 |
| 7,056,322 B2 | 6/2006 | Davison et al. | |
| 7,648,599 B2 * | 1/2010 | Berendt | 148/563 |
| 2003/0055314 A1* | 3/2003 | Petitto et al. | 600/109 |
| 2004/0002710 A1* | 1/2004 | Han et al. | 606/72 |
| 2004/0230193 A1 | 11/2004 | Cheung et al. | |
| 2005/0107791 A1 | 5/2005 | Manderson | 606/62 |

FOREIGN PATENT DOCUMENTS

| | | |
|---|---|---|
| DE | 19708279 | 9/1998 |
| WO | WO95/24870 | 9/1995 |
| WO | WO2005/094705 | 10/2005 |
| WO | WO 2006/120355 | 11/2006 |

OTHER PUBLICATIONS

Ankle Arthrodesis Nail Surgical Technique, Biomet, Inc., Form No. Y-BMT-596R/021500/H, © 2000 Biomet, Inc. Warsaw, IN.

Panta™ Arthrodesis Nail. Datasheet [online]. Integra LifeSciences Corporation, 2006, [retrieved on Jan. 12, 2007]. Retrieved from the Internet: <http://www.ilstraining.com/Mid%20%20Hindfoot%20Solutions/panta/panta_00.html>.

Retronail Ankle Arthrodesis Arthritic Deformity, Fractures, Failed Fusion. Products [online]. © 2007 orthofix.com, [retrieved on Apr. 4, 2007]. Retrieved from the Internet: <http://www.orthofix.com/products/retronail.asp?cid=5>.

T2™ TIBIAL Nailing System. Operative Technique. Stryker, pp. 1-31.

Tibiotalocalcaneal Nailing System Options Made Easy. Surgical Technique. Stryker, 2006. pp. 1-19.

Andreasen et al., *Laboratory and Clinical Analyses of Nitinol Wire*, American Journal of Orthepedics, vol. 73, No. 2, pp. 142-151 (Feb. 1978).

Cragg et al., *A New Percutaneous Vena Cava Filter*, American Journal of Roentgenology, vol. 141, pp. 601-604 (Sep. 1983).

Wasilewski, R., *Stress-Assisted Martensite Formation in TiNi*, Scripta Metallurgica, vol. 5, No. 2, pp. 127-130 (1971).

Watanabe, K., *Studies on New Superelastic NiTi Orthodontic Wire (Part 1) Tensile and Bend Test*, Dental Material and Devices Magazine, vol. 23, No. 61, pp. 1-61 (1982).

Results of the Partial International Search from corresponding PCT Application No. PCT/US2008/055188.

Extended European Search Report from related European Patent Application No. 06758489.6, dated Mar. 4, 2010.

International Search Report, PCT/US06/15207.

El Feninat, Fatiha et al., *Shape Memory Materials for Biomedical Applications*, Advanced Engineering Materials 2002, 4, No. 3, pp. 83, 86, 91-104.

Gall, Ken et al., *Thermomechanics of the shape memory effect in polymers for biomedical applications*, 2005 Wiley Periodicals, Inc., pp. 339-348.

Gall, Ken et al., *Shape-Memory Polymers for Microelectromechanical Systems*, Journal of Microelectromechanical Systems, vol. 13, No. 3, Jun. 2004, pp. 472-483.

Gall, Ken et al., *Shape memory polymer nanocomposites*, Acta Materialia 50, (2002), pp. 5115-5126.

Jeon, HG et al., *Shape memory and nanostructure in poly(norbornyl-POSS) copolymers*, Polymer International, Polym Int 49 (2000), pp. 453-457.

Langer, Robert et al., *Designing materials for biology and medicine*, Nature, vol. 428, Apr. 1, 2004, pp. 487-492.

Lendlein, Andreas et al., *Light-induced shape-memory polymers*, Nature, vol. 434, Apr. 14, 2005, pp. 879-882.

Lendlein, Andreas et al., *Biodegradable, Elastic Shape-Memory Polymers for Potential Biomedical Applications*, Science, vol. 296, May 31, 2002, pp. 1673-1676.

Lendlein, Andreas et al., *AB-polymer networks based on oligo (ε-caprolactone) segments showing shape-memory properties*, PNAS, Jan. 30, 2001, vol. 98, No. 3, pp. 842-847.

Lin, J. R. at al., *Study on Shape-Memory Behavior of Polyether-Based Polyurethanes. I. Influence of the Hard-Segment Content*, Journal of Applied Polymer Science, vol. 69, (1998), pp. 1563-1574.

Lin, J.R. et al., *Study on Shape-Memory Behavior of Polyether-Based Polyurethanes. II. Influence of Soft-Segment Molecular Weight*, Journal of Applied Polymer Science, vol. 69, (1998), pp. 1575-1586.

Liu, Changdeng et al., *Chemically Cross-Linked Polycyclooctene: Synthesis, Characterization, and Shape Memory Behavior*, Macromolecules, 2002, 35, pp. 9868-9874.

Liu, Yiping et al., *Thermomechanics of shape memory polymers: Uniaxial experiments and constitutive modeling*, International Journal of Plasticity, 22 (2006), pp. 279-313.

Liu, Yiping et al., *Thermomechanical recovery couplings of shape memory polymers in flexure*, Institute of Physics Publishing, Smart Mater. Struct. 12 (2003), pp. 947-954.

Maitland Ph.D., Duncan J. et al., *Photothermal Properties of Shape Memory Polymer Micro-Actuators for Treating Stroke*, Lasers in Surgery and Medicine 30 (2002), pp. 1-11.

Metcalfe, Annick et al., *Cold hibernated elastic memory foams for endovascular interventions*, Biomaterials 24 (2003), pp. 491-497.

Metzger, Melodie F. et al., *Mechanical Properties of Mechanical Actuator for Treating Ischemic Stroke*, Biomedical Microdevices, vol. 4, No. 2, May 2002, pp. 89-96.

Smith, Thor L., *Strength of Elastomers-A Perspective*, Polymer Engineering and Science, vol. 17, No. 3, Mar. 1977, pp. 129-143.

Smith, Thor L., *Ultimate Tensile Properties of Elastomers. I. Characterization by a Time and Temperature Independent Failure Envelope*, Journal of Polymer Science: Part A, vol. 1, No. 12 (1963), pp. 3597-3615.

Smith, Thor L. et al., *Time and Temperature Dependence of the Ultimate Properties of an SBR Rubber at Constant Elongations*, Journal of Applied Physics, vol. 31, No. 11, Nov. 1960, pp. 1892-1898.

Takahashi, Toshisada et al., *Structure and Properties of Shape-Memory Polyurethane Block Copolymers*, Journal of Applied Polymer Science, vol. 60, (1996), pp. 1061-1069.

Tobushi, H. et al., *Thermomechanical Constitutive Modeling in Shape Memory Polymer of Polyurethane Series*, Journal of Intelligent Material Systems and Structures, vol. 8, Aug. 1997, pp. 711-718.

Tobushi, Hisaaki, et al., *Thermomechanical properties in a thin film of shape memory polymer of polyurethane series*, Smart Mater. Struct. 5 (1996), pp. 483-491.

Wache, H.M. et al., *Development of a polymer stent with shape memory effect as a drug delivery system*, Journal of Materials Science: Materials in Medicine 14 (2003), pp. 109-112.

Yahia, L., (Ed.), *Shape Memory Implants*, Springer-Verlag Berlin Heidelberg New York, 2000, (complete book—out of print).

Yakacki, Christopher M. et al., *Strong and Biocompatible Shape Memory Polymers for Soft Tissue Orthopedic Fixation*, Submitted to Nature Materials, 2006, pp. 1-27.

Zhu, G. et al., *Shape-Memory Effects of Radiation Crosslinked Poly(ε-caprolactone)*, Journal of Applied Polymer Science, vol. 90, (2003), pp. 1589-1595.

* cited by examiner

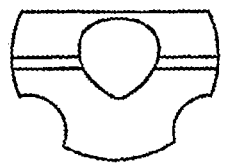
FIG.5I
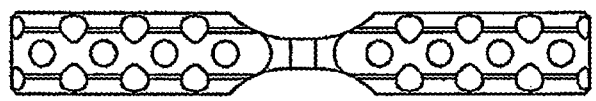
FIG.5B
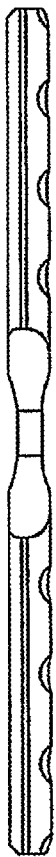
FIG.5F
FIG.5H
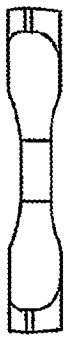
FIG.5G
FIG.5C
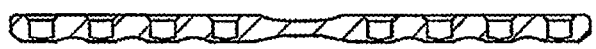
410
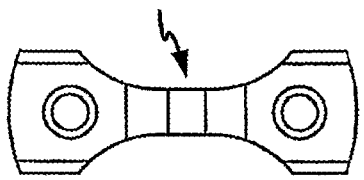
FIG.5D
420
FIG.5E
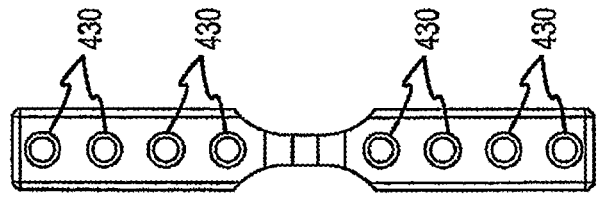
430 430 430 430
FIG.5A THE STRESS-STRAIN DIAGRAM FOR
LIVING TISSUES AND A NiTi ALLOY [1].

$A = F_R/\sigma_R$ (1) $L = \Delta L/\varepsilon$ (2)

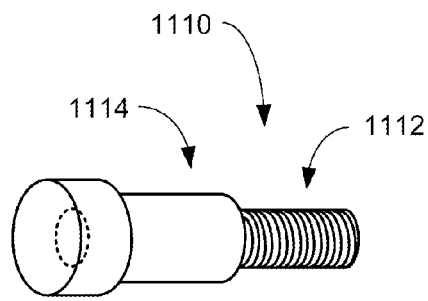
Fig. 11
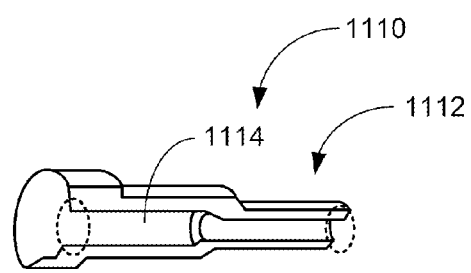
Fig. 11B
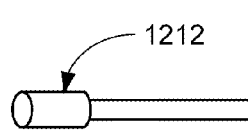
Fig. 12
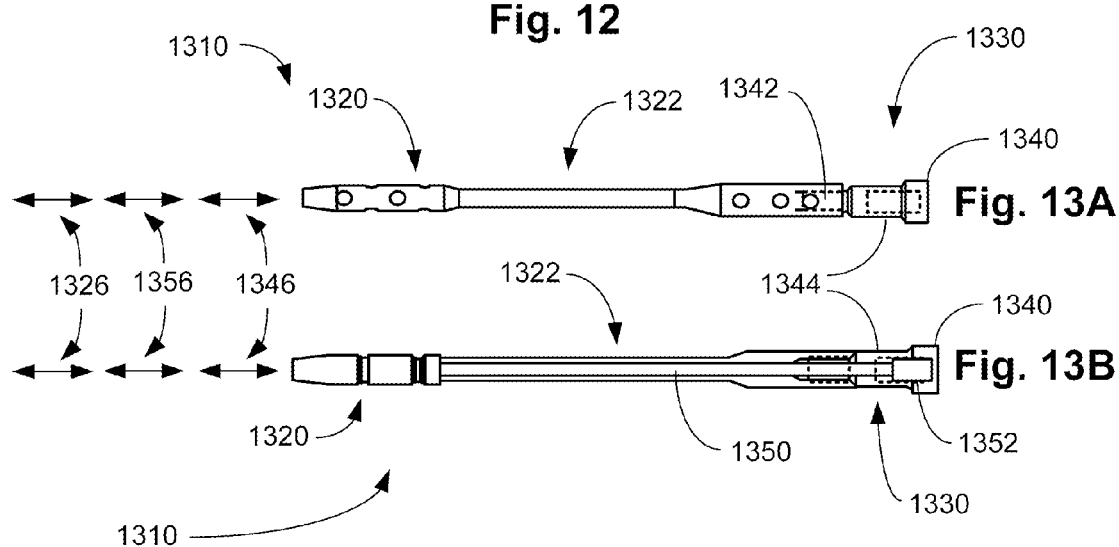
Fig. 13A
Fig. 13B
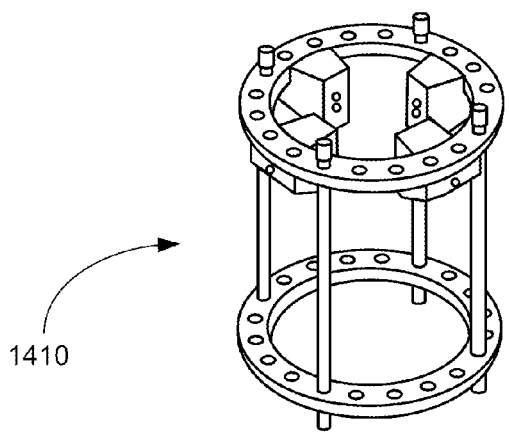
Fig. 14

2210

2220

2310

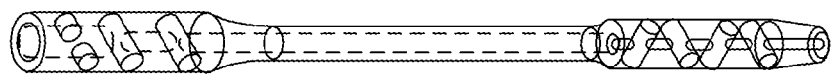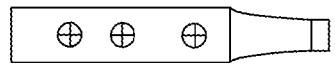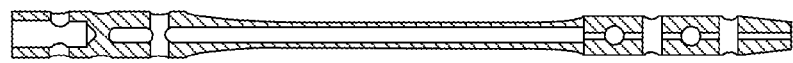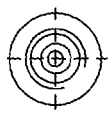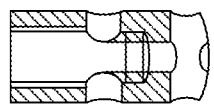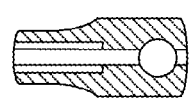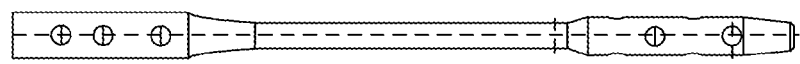

OSTEOSYNTHETIC IMPLANTS AND METHODS OF USE AND MANUFACTURE

CROSS-REFERENCES TO RELATED APPLICATIONS

The present application is a national stage entry of PCT/US06/15207, which is a continuation-in-part of Ser. No. 11/112,865, filed on Apr. 21, 2005 now U.S. Pat. No. 7,985,222, which claims priority from U.S. Provisional Application 60/563,952 filed on Apr. 21, 2004 the complete disclosures of which are incorporated herein by reference for all purposes.

BACKGROUND OF THE INVENTION

The present application relates generally to bone fracture repair, and more specifically, to osteosynthetic implants for fracture repair and methods of their use and manufacture.

In 1959, a group of Swiss Orthopedic and General Surgeons formed the Arbeitsgemeinschaft fur Osteosynthesefragen (AO), also known as the Association for the Study of Internal Fixation (ASIF). The AO/ASIF is now a multi-national group of doctors and scientists with the expressed purpose of studying bone healing and continuous development of fracture fixation techniques for patient care. In the United States, as well as most other countries, AO/ASIF guidance regarding skeletal fixation has become the standard of care for traumatic fracture as well as therapeutic osteotomy fixation techniques. It is under these AO/ASIF guidelines that the surgeon plans and carries out procedures to achieve the desired end result of bone healing and skeletal function.

Problems can arise when the bone fracture or fusion site is not sufficiently stabilized during the healing timeframe. Depending on the nature of the fracture, screws and plates may be used alone, or in combination. One objective of osteosynthetic implants is the anatomic reduction of the fracture. Another objective would be to minimize or eliminate interfragmentary motion. Still another objective involves increasing or maximizing blood supply to the fracture site by reducing or minimizing additional vascular damage. Sustained compressive therapy can also be osteoinductive, due to its piezoelectric effects on osteoblasts themselves. Excessive interfragmentary motion results in the formation of fibrous, unmineralized scar tissue (resulting in a non-union or pseudoarthrosis) versus the regeneration of bone. The unmineralized scar tissue is not load supporting and skeletal function is lost. A sufficient blood supply must be maintained to support skeletal metabolism, bone regeneration, and remodeling of the fracture site. The current standard of care includes osteosynthetic devices that are made of either stainless steel or titanium.

The use of stainless steel or titanium in osteosynthetic devices has a long history and reasonable record of success. Over time, however, the stainless steel and titanium fixation constructs (both screws and plates) do not maintain compression across the fracture fragments. The reduction of compression of certain standard material constructs has been observed to be thirty-two percent (32%) over a two week period. As the necrotic surfaces of the fracture are resorbed, a non-load bearing gap develops between the fragments, thereby decreasing compression and increasing the risk of interfragmentary motion and scar tissue formation. Loss of compression is contrary to the objectives of fracture fixation in general, and osteosynthetic implants in particular. Improvements are desired to help maintain compressive load across the fracture site over a longer period of healing.

BRIEF SUMMARY OF THE INVENTION

The present application relates generally to bone fracture repair and bone fusion, and more specifically, to osteosynthetic implants for fracture/fusion repair and methods of their use and manufacture. Fracture repair devices, systems and methods include those for repairing intentional fracture sites, such as but not limited to osteotomies, for reconstructive purposes. Bony fusions of surgically resected joints throughout the body are included as well within the scope of the present invention. Fracture fixation devices, systems and methods of the present invention help maintain compressive loads across the fracture site for longer periods of time compared to prior devices. In some embodiments, the use of shape memory materials, including nickel titanium, delivers improved fracture repair characteristics. The present invention further includes methods of use and methods of manufacture of such bone fixation devices and systems.

In one embodiment, a bone fixation device according to the present invention includes an elongate element having a responsive zone. The elongate element is a plate, a nail, or a bone screw in alternative embodiments. The elongate element is adapted to be coupled to the bone so that the responsive zone is positioned adjacent a fracture or fusion site in the bone. The responsive zone is adapted to apply a desired pressure to the bone when coupled thereto. In a preferred embodiment, the responsive zone comprises a shape memory material, which may be nickel titanium or Nitinol.

In some embodiments, the elongate element comprises nitinol, while in other aspects, the responsive zone is pseudoelastic at a body temperature. In this manner, the elongate element may be used to apply desired forces at the fracture site. In some embodiments, the responsive zone is generally centrally located in the elongate element. In one aspect, the responsive zone has a smaller overall cross section than a cross section of an end of the elongate element. Such a configuration helps locate the stresses or pressures at a desired location within the elongate element, and more specifically, at the responsive zone.

In some aspects, the bone fixation device further includes a coupler adapted to couple the elongate element to the bone. The coupler may include one or more bone screws, which in some embodiments comprise a shape memory material. In a particular embodiment, the elongate element has first and second end sections each with at least one hole adapted to receive a coupler therethrough to couple the element to the bone. Other embodiments may use two, three, four, or more holes in one or both end sections to fixedly couple the device to the fractured bone.

The present invention further provides bone fixation systems. In one embodiment, the system includes an elongate element having a responsive zone of shape memory material, for example in its pseudoelastic state, and a coupler adapted to couple the elongate element to the bone so that the responsive zone is positioned adjacent a fracture site in the bone. In some embodiments, the system includes a removable clamp, with the clamp adapted to maintain the elongate element responsive zone in a desired position prior to coupling of the element to the bone, and may further be adapted to be removed from the elongate element after coupling of the element to the bone. In one aspect, the responsive zone is adapted to apply a desired pressure to the bone when the elongate element is coupled to the bone.

The present invention further provides methods of stabilizing a fractured bone. In one such embodiment, the method includes providing an elongate element, which may be a plate, an intermedullary or intramedullary nail, a bone screw, a pin, or related devices. The elongate element has a responsive zone of a shape memory material, with the responsive zone adapted to apply a desired pressure to the bone when coupled thereto. The method includes coupling the elongate element to the bone so that the responsive zone is positioned adjacent a fracture site in the bone.

In one aspect, the method includes applying a force to the elongate element to lengthen the responsive zone a desired amount, maintaining the element in the lengthened position, coupling the element to the bone so that the lengthened responsive zone is positioned adjacent the fracture site, and releasing the elongate element. In some aspects, a clamp is used to maintain the element in the lengthened position. In this manner, the elongate element may be released by removing the clamp. As a result, the stress formed in the responsive zone can be applied to the bone to facilitate fracture and fusion site compression, stability, healing, and the like.

In a particular aspect, coupling the elongate element to the bone includes attaching a first coupler to the element and to the bone on a first side of the fracture site, and attaching a second coupler to the element and to the bone on a second side of the fracture site. In this manner, the responsive zone is positioned adjacent the fracture site. In one aspect, the force applied to the elongate element to lengthen the responsive zone the desired amount corresponds to a desired compressive force to be applied to the fractured bone when the element is coupled thereto. Again, the shape memory material may be nitinol, or other shape memory materials compatible with the human body.

In one aspect, embodiments of the present invention provide a bone fixation system. The sytem can include a bone fixation device having a responsive zone, and a clamp configured to be received at least partially within an internal lumen of the bone fixation device, where the internal lumen disposed along an axial length of the bone fixation device. The clamp can be adjustable between a first mode that induces or maintains a first amount of strain in the responsive zone along the axial length of the bone fixation device, and a second mode that induces or maintains a second amount of strain in the responsive zone along the axial length of the bone fixation device. The clamp may be removably coupled with the bone fixation device. In some instances, the clamp includes an end cap and an internal brace. The end cap can be adjustably engaged with the bone fixation device at an end cap first section, and adjustably engaged with the internal brace at an end cap second section. Relatedly, the end cap can be threadably engaged with the bone fixation device at an end cap first section, and i threadably engaged with the internal brace at an end cap second section. In some aspects, a central longitudinal axis defined by the internal lumen of the bone fixation device is collinear with a central longitudinal axis defined by the internal brace. In related aspects, the central longitudinal axis defined by the lumen of the bone fixation device is collinear with a central longitudinal axis defined by the end cap.

The bone fixation device can be, for example, an intramedullary or intermedullary nail, a screw, a plate, a pin, a compression rod, a vertebral fixation device, and the like. The responsive zone can have a physical characteristic similar to human tissue. In some cases, the physical characteristic is a modulus such as an elastic modulus. For example, the modulus can have a value in a range from between about 10 GPa to about 70 GPa. In some cases, the human tissue is bone. Often, the responsive zone includes a shape memory material, which may be a shape memory alloy. A shape memory alloy can include a nickel alloy, a copper alloy, and the like. In some cases, the shape memory alloy includes a nickel titanium alloy, a copper zinc aluminum alloy, a copper aluminum nickel alloy, or the like. The responsive zone is configured to provide a predetermined or preset compressive force across a bone fracture or fusion site when the clamp is removed or inactivated. Similarly, the responsive zone can be configured to recover to a predetermined or preset length when the clamp is removed or inactivated.

In another aspect, embodiments provide a bone fixation device that includes a machined responsive zone having a hardness value within a range from about 5 HRB to about 60 HRC on the Rockwell B and C Hardness Scales. The responsive zone may include a nickel titanium alloy. In still another aspect, embodiments provide a method of preparing a bone fixation system. The method can include providing a bone fixation device having a responsive zone, inserting a clamp at least partially within an internal lumen of the bone fixation device, where the internal lumen disposed along an axial length of the bone fixation device, and inducing, maintaining, controlling, or modulating a strain in the responsive zone along the axial length of the bone fixation device with the clamp. Such methods can also include threadably engaging an end cap of the clamp with the bone fixation device at an end cap first section, and threadably engaging the end cap with an internal brace of the clamp at an end cap second section.

In yet another aspect, embodiments include methods of deploying a bone fixation device in a patient. Such methods can include, for example, providing a bone fixation device having a first portion, a second portion, and a responsive zone disposed therebetween, and inserting a clamp at least partially within an internal lumen of the bone fixation device. The internal lumen can be disposed along an axial length of the bone fixation device. The method may also include inducing, maintaining, controlling, or modulating a strain in the responsive zone along the axial length of the bone fixation device with the clamp, coupling the bone fixation device with a bone of the patient by attaching the first portion of device to a first bone location, and attaching the second portion of the device to a second bone location. The bone typically includes a fracture or fusion site disposed between the first and second bone locations. The method can further include securing the bone fixation device to an external brace assembly, removing the clamp from the bone fixation device, and removing the external brace assembly from the bone fixation device. The bone fixation device can remain coupled with the patient's bone, and the responsive zone can be allowed to relax so as to transmit a compressive force to the fracture or fusion site of the patient's bone via the bone fixation device.

In one aspect, embodiments include methods of processing a shape memory material for use in a bone fixation device. Methods may include, for example, treating the shape memory material with a first treatment to transform the shape memory material from a first state to a second state, machining the shape memory material while it is in the second state, and treating the machined shape memory material with a second treatment to transform the shape memory material from the second state to the third state. The first treatment may include a first heat cycle of at least 5 minutes at a temperature of about 600° C. The first treatment may also include a second heat cycle of at least 5 minutes at a temperature within a range from between about 200° C. to about 550° C. In some embodiments, the first state has a first hardness value, the second state has a second hardness value, and the first hardness value is between about 100% and about 500% of the second hardness value. The first state can have a first shape recovery value, the third state can have a third shape recovery value, and the third shape recovery value may be at least 95% of the first shape recovery value. In some cases, the shape memory material includes a shape memory alloy such as a nickel titanium alloy, a copper zinc aluminium alloy, or a copper aluminium nickel alloy. The third state may have an optimal pseudoelastic property profile for the shape memory material. In some aspects, the first state can have a first hardness value, the third state can have a third hardness value, and a difference between the first hardness value and the third hardness value may be less than about 3 HRC on the Rockwell C Hardness Scale. In some cases, the difference may be less than about 10 HRC.

In another aspect, embodiments encompass methods of preparing a bone fixation device. Methods may include providing a bone fixation device comprising a shape memory material, and machining the shape memory material while the temperature of the shape memory material is maintained at or above an austenitic transition temperature. In some aspects, the shape memory material remains in a stiff austenite phase and does not transition to a malleable austenite phase during the machining.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

FIG. 5A is an overall view of the bone fixation device shown in FIG. 4;

FIGS. 5B-5I are additional views of the fixation device shown in FIG. 5A, including a bottom view (FIG. 5A), a top view (FIG. 5B), a longitudinal cross-sectional view (FIG. 5C), a close-up bottom view of an expansive zone (FIG. 5D), an end view (FIG. 5E) and a side view (FIG. 5F);

FIGS. 11 and 11B illustrate an end cap according to embodiments of the present invention.

FIG. 12 shows an internal brace according to embodiments of the present invention.

FIGS. 13A and 13B show a bone fixation system according to embodiments of the present invention.

FIG. 14 shows a jig or external fixation device according to embodiments of the present invention.

FIGS. 24A to 24H show a prototypical intramedullary nail having exemplary dimensions.

DETAILED DESCRIPTION OF THE INVENTION

It has been determined that when a bone is set and a compressive force is applied to the fracture or fusion fixation device, the force between the fragments ends decreases rapidly as a function of time. Ideally, the fixation device is able to maintain a compressive force, which will allow for the continuation of healing through reduction of the fracture gap, and stability of the fracture gap. If this does not occur, a loss of compression may be followed by the lack of union and stability of the fracture site, which in turn reduces the healing. A fracture fixation device is put in place to stabilize the fracture site, however, if the compressive force is not present then micro-motion between the fracture ends may occur. This, in turn, may cause unnecessary resorption, which will lead to non-union of the bone or the presence of large voids. These reasons show the importance of a device to actively match the changes in the body, as well as have a similar response as bone.

Embodiments of the present invention include bone fixation devices, including plates, bone nails such as intramedullary nails, bone screws, and the like, that can provide sustained compression (spontaneous dynamic compression) across a bone fracture over time. The dynamic compressive forces are stable or generally stable as a function of bone surface resorption at the fracture site, facilitating improved bone healing and reducing non-union rates. Some bone fixation devices of the present invention will allow for approximately six percent (6%) relaxation before compressive force loss. In contrast, typical stainless steel or titanium bone screws lose their compressive forces after about one percent (1%) resorption at the fracture surface.

Figure 1A:
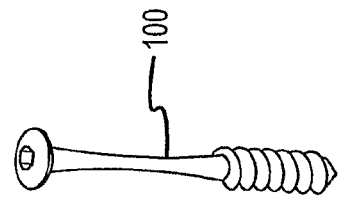
FIG. 1A is an overall view of a dynamic compression bone screw according to an embodiment of the present invention.
Figure 1C:
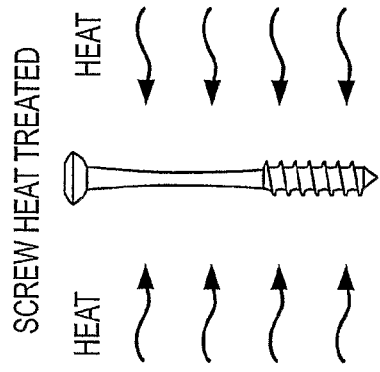
FIGS. 1B and 1C are simplified views of steps for forming the dynamic compression bone screw depicted in FIG. 1A.
Figure 1B:
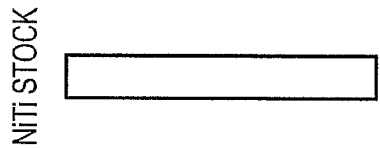

FIGS. 1A-2C depict a dynamic compression bone screw 100 according to an embodiment of the present invention. Bone screw 100 shown in FIG. 1A is further described in conjunction with FIGS. 3A-3F. In a particular embodiment, bone screw 100 is formed from nickel titanium, a shape memory alloy referred to as Nitinol. As shown in FIGS. 1B and 1C, screw 100 is formed from a Nitinol stock or block, and may be heat treated to produce desired characteristics. Shape memory alloys, such as Nitinol, exhibit the capacity to recover relatively large strains (e.g., about 6%) by the application of heat (shape memory) or by gradual unloading (pseudo-elasticity). The present invention exploits the large strain capacity and recovery behavior of shape memory alloys such as Nitinol for bone repair with novel devices, systems, and methods. In one embodiment, the fixation devices, such as screw 100, are machined from a shape memory material such as Nitinol that is thermally treated to exhibit pseudo-elasticity at body temperature. The overall screw geometry, responsive element geometry, and material heat treatment will be specified to sustain the necessary compressive forces as a function of fracture or fusion site conditions.

The shape memory effect of Nitinol is the temperature-induced transformation between the malleable martensite (lower temperature) phase and the more rigid austenite phase (higher temperature) that exhibits the desired pre-set shape. Exploitation of the thermally driven phase change helps some embodiments of the present invention deliver desired bone fixation results. The pseudoelastic effect of Nitinol refers to the return to its pre-set austenite configuration upon unloading after elastic deformation. The initiation of superelastic behavior of Nitinol requires the formation of stress induced martensite (SIM) from the austenite phase, such as by the application of an external load or stress. Reduction of the external load or stress induces formation of the austenite phase and hence its pre-set configuration. Nitinol is able to accumulate large deflection (strain) at a nearly constant load (stress). The relatively flat region of the Nitinol load-to-deflection relationship can be used for some devices of the present invention.

Figure 9A:
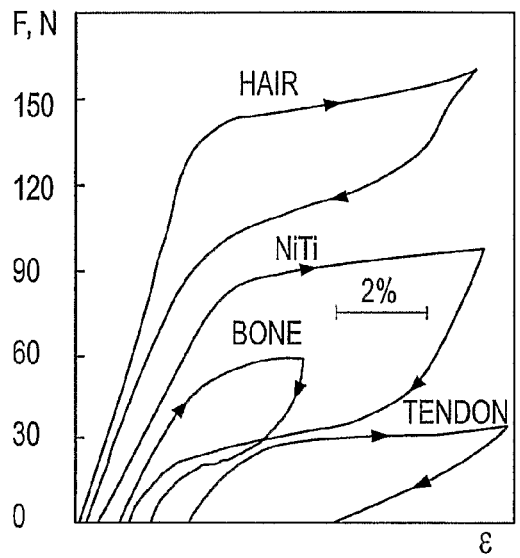
FIGS. 9A and 9B are graphical views of material properties of bone fixation screws and devices according to an embodiment of the present invention.

Some embodiments of the present invention take advantage of the stress/strain (modulus) of NiTi, depicted in FIG. 9A. Such characteristics of NiTi are beneficial in the development and use of improved total joint implants, for example. This property of NiTi decreases overall bone to implant interface stresses, resulting in a longer implant lifetime. Embodiments of the present invention, particularly those using NiTi, help the bone maintain load, which increases healing and helps smaller implants to maintain the same or similar stability as larger ones in similar areas of fixation by reducing stress/strain and sheering forces.

Formation of SIM phase within a responsive zone of screw 100, or other osteosynthetic implants and devices, may be achieved prior to surgical placement or as a result of surgical placement. For the bone screws 100 depicted in FIG. 1A, the responsive zone of screw will be designed to initiate SIM formation as a result of the installation process. This occurs, at least in part, due to the elongating forces applied to the screw when the screw is used. Additional details on the responsive zone are discussed in conjunction with FIGS. 3A-3F.

Figure 2C:
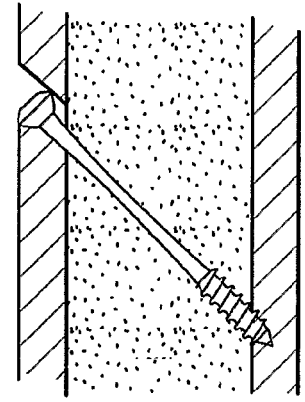
FIGS. 2A-2C schematically depict the use of the dynamic compression bone screw of FIG. 1A for repairing a bone fracture.
Figure 2B:
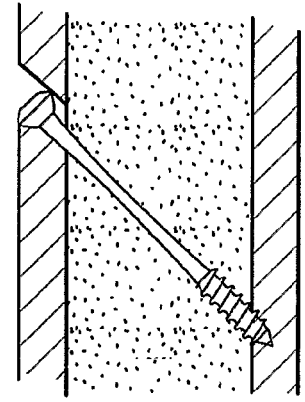
Figure 2A:
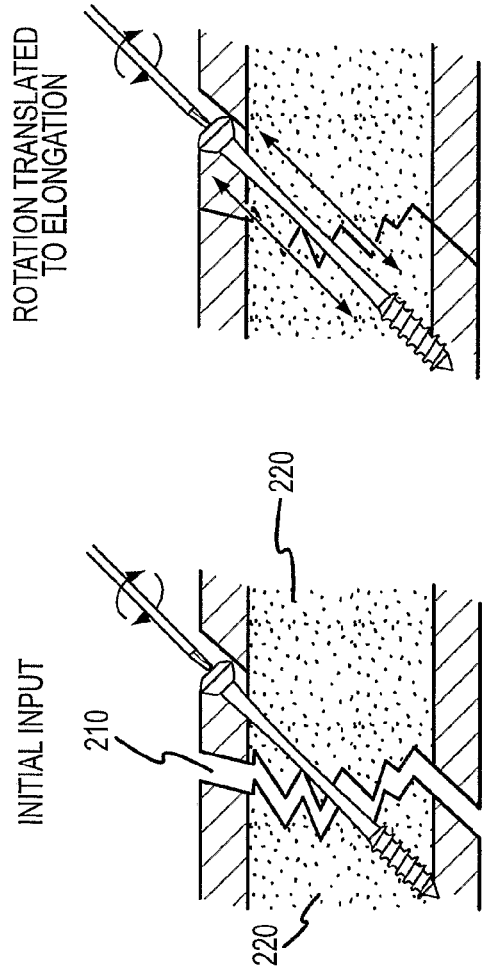

One technique for fracture fixation is the placement of a lag screw across the appositional ends of a break in the bony cortex. Inserting the screw across the fracture site helps generate the dynamic force capacity in the screw. As shown in FIG. 2A, bone screw 100 is inserted at an angle relative to a fracture site 210. Screw 100 is rotated to draw the two bone fragments 220 towards one another, creating a compressive force therebetween. The rotational torque used to turn screw 100 is translated into axial compression between bone fragments 220. The result is the proper alignment of bone fragments 220 as shown in FIG. 2B. Screw 100 maintains a compressive force on bone fragments 220 for a much longer period of time than traditional bone screws formed of steel, titanium, or the like. As a result, a more fully healed fracture site 210 results (FIG. 2C). During healing and bone absorption, the force generated by prior-art screws can decrease leaving a less compressive force acting across the fracture site 210 over time. In contrast, bone screws 100 of the present invention are a dynamic screw that can maintain higher compression values over a longer course of healing. Advantages of screw 100 includes better promotion of direct bone healing, reduction in non-union rates in high risk fracture sites, and a reduction in bone implant site resorption. In some embodiments, at least some of these advantages are achieved by the use of a shape memory material, such as Nitinol, and its inherently similar stress/strain properties to those of bone.

FIG. 3A-3F depict further details on bone screw 100 according to an embodiment of the present invention. It will be appreciated by those skilled in the art that FIGS. 3A-3F depict a particular example, and the present invention is not limited to the dimensions and configurations shown therein. As can best be seen in FIGS. 3A, 3D, and 3F, bone screw 100 has a shank portion 110 with a diminished thickness or radius compared to the radius or thickness of a threaded portion 120 or of a head 130. In this manner, the reduced area of shank portion 110 allows for a stress concentration to be localized over shank portion 110, which allows shank portion 110 to elongate to form a responsive element or zone. In one embodiment, the elongation of shank portion 110 occurs during the insertion process into the fractured bone, as depicted in FIG. 2B. By using the responsive element or shank portion 110, bone screw 100 is able to localize the force caused by the SIM over the fracture site. The non-responsive screw portions, such as head 130, stays generally strain-free and contributes little force to the bone due to SIM.

Figure 3F:
FIG. 3F is an overall view of the bone screw depicted in FIG. 3A.
Figure 3D:
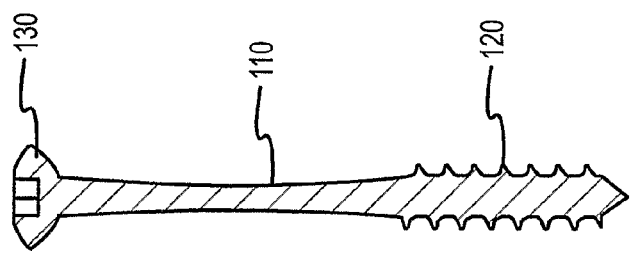
FIG. 3D is a longitudinal cross-sectional view of the bone screw depicted in FIG. 3A.
Figure 3B:
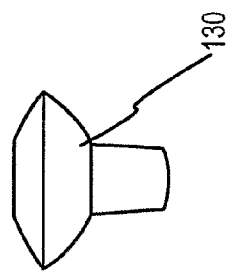
FIGS. 3B and 3C are close-up views of the screw head and threaded portion, respectively, for the bone screw depicted in FIG. 3A.
Figure 3C:
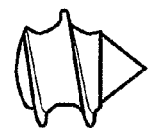
Figure 3A:
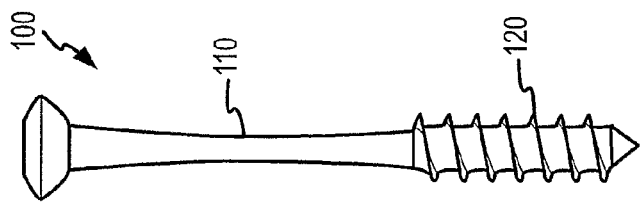
FIG. 3A is a side view of the dynamic compression bone screw of FIG. 1A.
Figure 3E:
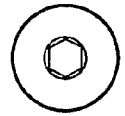
FIG. 3E is a top view of the bone screw depicted in FIG. 3A.
Figure 3G:
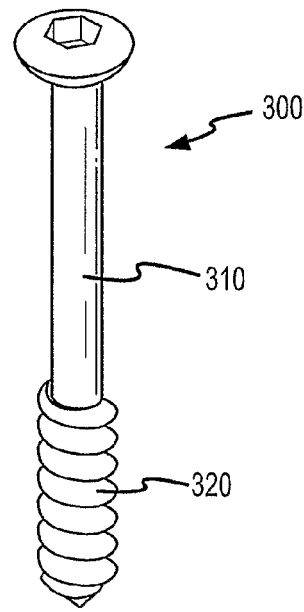
FIG. 3G is an overall view of a dynamic compression bone screw according to an alternative embodiment of the present invention.

In an alternative embodiment, a bone screw 300 depicted in FIG. 3G has a generally uniform diameter through a shank portion 310. In this embodiment, only shank portion 310 is formed of a shape memory material, with threaded end portion 320 comprising a stiffer region less susceptible to elongation.

Figure 4:
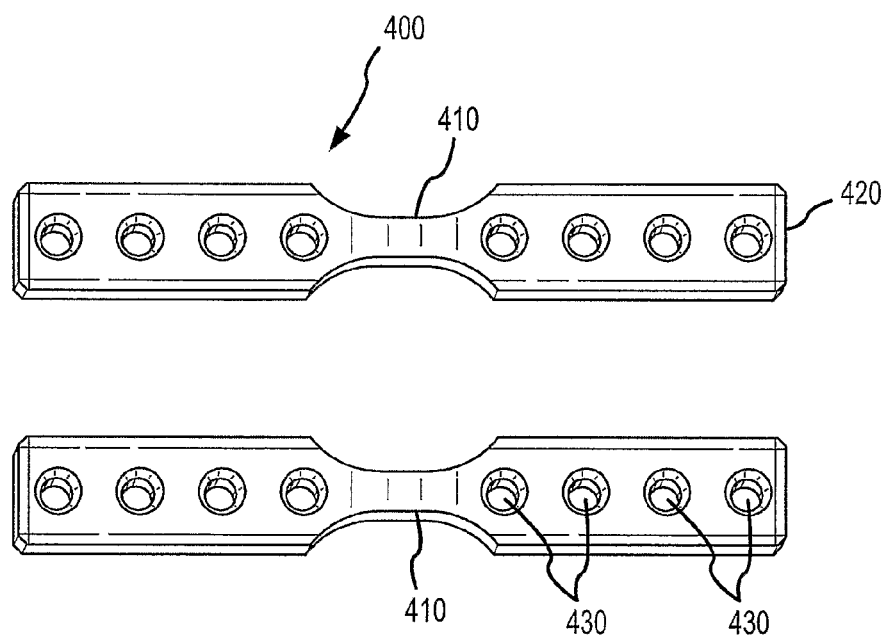
FIG. 4 is an overall view of two bone fixation devices according to an embodiment of the present invention.

Turning now to FIG. 4, a bone fixation device 400 according to an embodiment of the present invention will be described. Bone fixation device 400 allows for a longer and greater sustained compressive force. For example, current bone plates applied to a fractured surface tend to lose compressive force within two days to two weeks after surgery, thus slowing the healing process. Additional problems with prior-art plates, such as deflections and rigidness, also result in a greater chance of refracture and slow healing. In one embodiment of the present invention, bone fixation device 400 comprises a shape memory alloy, that may be Nitinol or the like. Fixation device 400 is a dynamic device that can change over time with the human body into which it is inserted. In a preferred embodiment, device 400 comprises Nitinol, due in part to its capacity to recover large strains over time. In one embodiment, this is accomplished through the creation of device 400 having a responsive zone section 410. In some embodiments, responsive zone 410 has a smaller overall cross-sectional area than the non-responsive zone(s) of device 400. Responsive zone 410 is used to localize the elongation of device 400 to that area. In one embodiment, device 400 is elongated based on the application of a force similar to or the same as the force required to stabilize the fracture to which device 400 is applied. Device 400 will be elongated based on the force required to stabilize the fracture and apply the necessary healing force. After device 400 has been elongated, in one embodiment it is held in an elongated state by an external clamp or similar structure to prevent recovery motion of device 400. After device 400 is affixed to the fracture site, the clamp, or other retaining mechanism can be removed. Further details on the use of device 400 are discussed in conjunction with FIGS. 7A and 7B.

FIGS. 5A-5I depict various views of device 400 or portions of device 400, according to particular embodiments of the present invention. Again, the dimensions, including the lengths, widths, thicknesses and radii of curvature, may vary within the scope of the present invention from those shown in the figures. More specifically, the figures include a longitudinal cross-sectional view (FIG. 5C), a top view (FIG. 5B), a bottom view (FIG. 5A), a side view (FIG. 5F), an end view (FIG. 5E), and a close-up bottom view of expansive zone 410 (FIG. 5D), of device 400. In a preferred embodiment, device 400 is coupled to a bone having a fracture site so that responsive zone 410 is disposed adjacent the fracture site. This arrangement can be seen in FIGS. 6A and 6B.

Figure 6A:
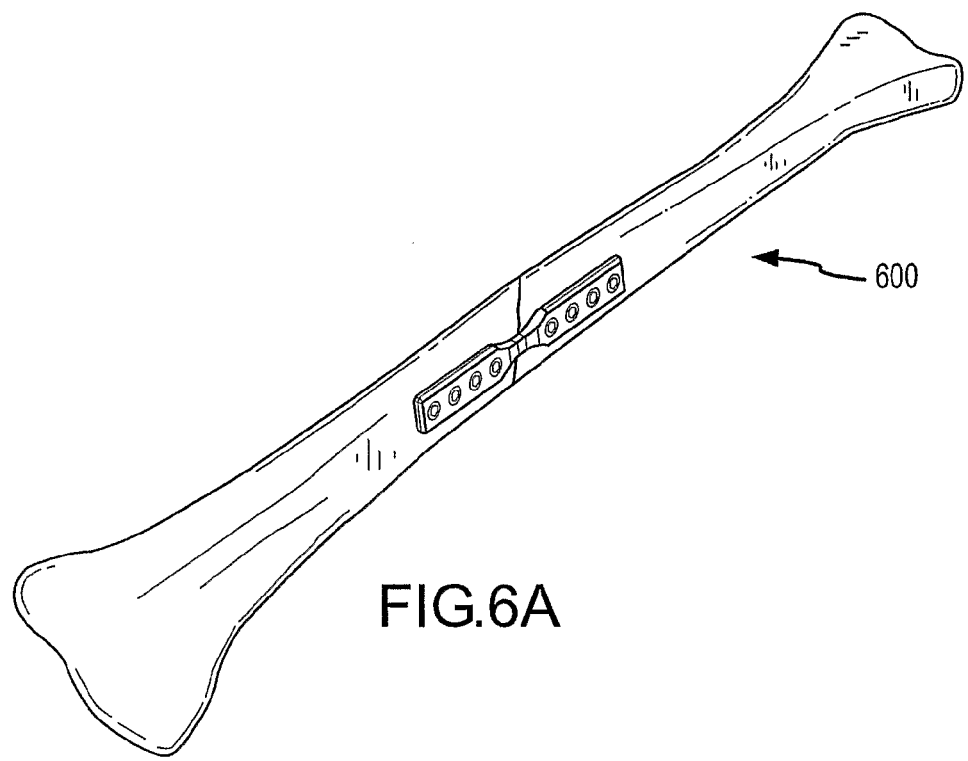
FIGS. 6A and 6B are overall views of a fixation device coupled to a bone having a fracture site.
Figure 6B:
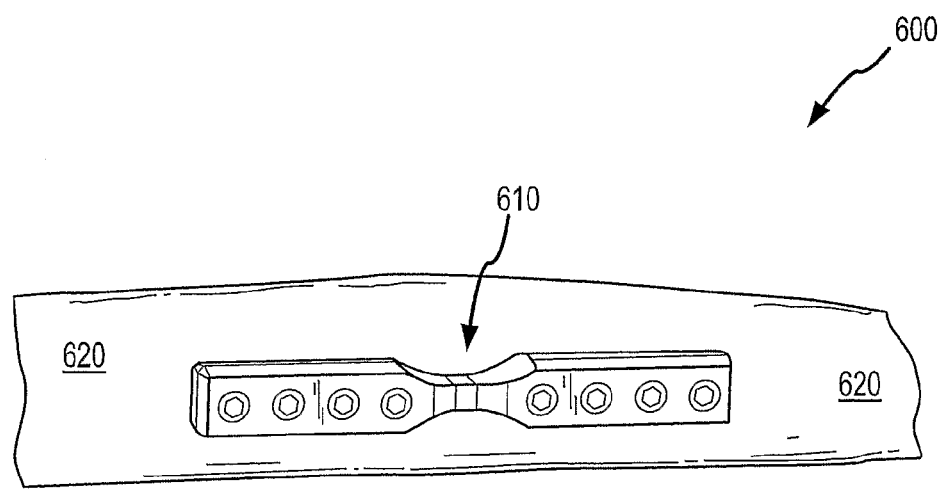

As shown, device 400 has one or more holes 430 disposed on each side of responsive zone 410 so that device 400 may be coupled to a fractured bone 600. While FIGS. 6A and 6B depict four holes 430 on each side of the fracture site, a greater or lesser number of holes 430 may be used within the scope of the present invention. In some embodiments, holes 430 are adapted to receive a screw or other fixation element to affix device 400 to bone 600. The coupling of device 400 to bone 600 preferably positions responsive zone 410 across or adjacent a bone fracture site 610. This may involve attaching one end of device 400 to one bone segment 620 and the second end of device 400 to the opposing bone segment 620. In some embodiments, the screw or fixation element used to couple device 400 to bone segment 620 comprises a bone screw, which may be made of stainless steel, titanium or the like. In a particular embodiment, screws or fixation elements used to coupled device 400 to bone 600 comprise a shape memory alloy, such as Nitinol.

Figure 7A:
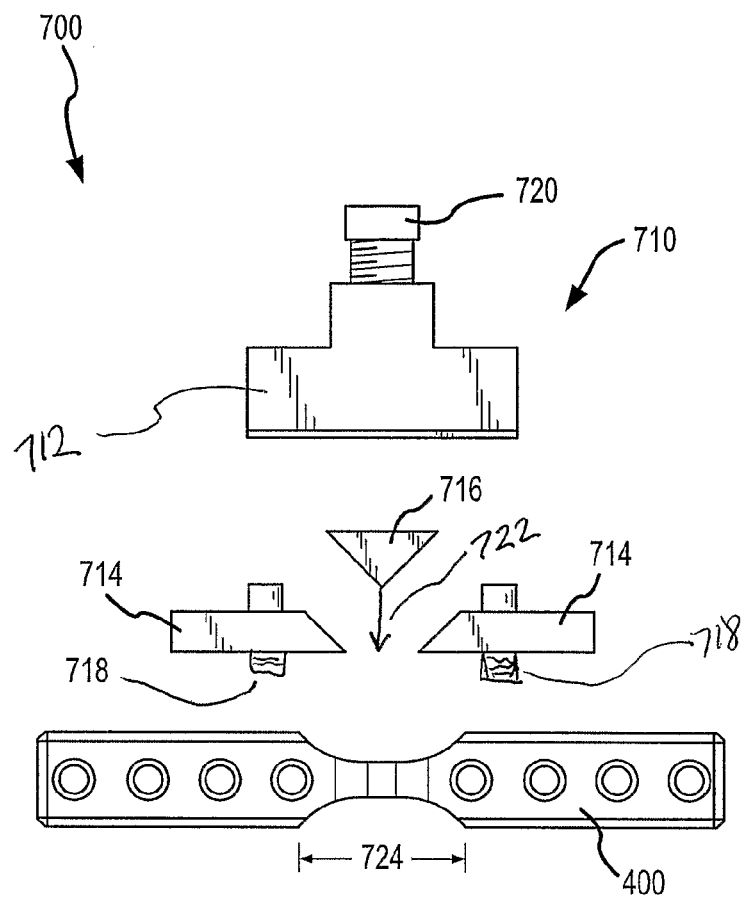
FIGS. 7A and 7B are exploded and assembled overall views, respectively, of a bone fixation system according to an embodiment of the present invention using the fixation device shown in FIG. 4.
Figure 7B:
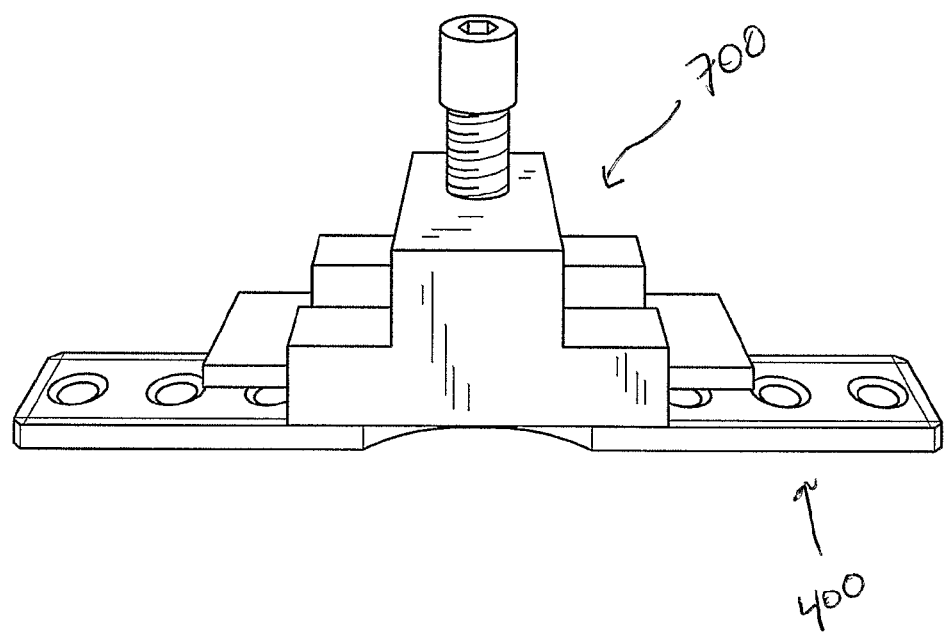

FIGS. 7A and 7B depict a bone fixation system 700 according to an embodiment of the present invention. System 700 includes fixation device 400 as previously described, and a clamp 710. While FIG. 7A depicts a single example of clamp 710, other clamp types fall within the scope of the present invention. Further, alternative devices may be used in lieu of clamp 710, provided the alternative devices are capable of attaching to device 400, and preferably are capable of holding device 400 in a desired position or elongated state. In operation, an elongating force is applied to device 400 to stretch or elongate device 400 to a prescribed length. As described further below, the application of the prescribed force is determined at least in part by the necessary force to provide healing effect to the bone to which device 400 will be applied. Once device 400 is elongated to the desired length, clamp 710 is used to maintain device 400 in the elongated position. Clamp 710 maintains the elongated position of device 400 until device 400 is attached to the fractured bone. Once device 400 is attached to the fractured bone, clamp 710 may be removed from device 400. In this manner, device 400 is attached to the fractured site and, upon the release of clamp 710, device 400 provides the desired compressive force through the fractured location. Again, in some embodiments device 400 comprises a shape memory material, and in a particular embodiment comprises Nitinol. Preferably, the application of the compressive force is of sufficient duration to facilitate healing as well as to avoid some or all of the other problems associated with prior-art devices constructed of stainless steel, titanium, or similar materials.

In the depicted embodiment, clamp 710 comprises a main component 712, first and second device-engaging components 714, and a wedge element 716. In one embodiment, device-engaging components 714 are disposed so that screws, lugs, posts or the like 718 extending from components 714 pass at least partially through corresponding holes 430 in device 400. Main component 712 is then coupled to device-engaging components 714 with wedge element 716 positioned therebetween. By rotating or depressing a pressure applicator 720, which in one embodiment is a screw, a force is applied to wedge 716. The application of a force to wedge 716 in the direction shown by arrow 722 causes an outward force to be applied to components 714, as shown by arrows 724. As can be seen in FIG. 7A, the force depicted by arrows 724 results in an elongating force being applied to device 400 through the use of screws, lugs, or posts 718. By controlling the physical relationship between pressure applicator 720 and components 714, the elongating force to device 400 may be controlled. The coupled configuration of clamp 700 with device 400 is generally depicted in FIG. 7B.

In another embodiment, a separate device or system is used to apply the elongating force to device 400. This may occur, for example, by pulling on opposing ends of device 400 to create an elongating force similar to that represented by arrows 724. Once device 400 has been elongated the desired amount, clamp 710 may be coupled to device 400 in the manner substantially as described above to hold device 400 in the elongated position. In this embodiment, pressure applicator 720 is operated so that the screws, lugs, or posts 718 engage holes 430 to hold device 400 in its desired elongated state. Again, device 400 is then coupled to bone 600, which preferably positions responsive zone 410 across or adjacent bone fracture site 610. This may involve attaching one end of device 400 to one bone segment 620 and the second end of device 400 to the opposing bone segment 620. Once device 400 is coupled to bone 600, clamp 700 is removed.

The present invention further provides bone fixation rods, nails and the like. In one embodiment, a bone fixation rod or nail 800 has a first end 810 and a second end 812, with a middle section 814 disposed therebetween. In one embodiment, some or all of rod 800 comprises a shape memory alloy, that in a preferred embodiment comprises Nitinol. For example, in one embodiment, middle section 814 comprises Nitinol. In this manner, middle section 814 is a responsive zone having the characteristics as generally described herein. In another embodiment, one or both of first end 810 and second end 812 comprise Nitinol. In still another embodiment, the entire rod 800 is Nitinol.

In one embodiment, rod 800 is a dynamic intramedullary nail. Such a device may be used, for example, in retrograde tibio-talo-calcaneal fusions. Nail 800 addresses fusion or fracture site compression problems, as described generally herein in conjunction with prior embodiments, as well as vascular preservation issues. For example, rod 800 may provide dynamic compression across a fusion site in a manner that allows for the use of smaller rods 800, or nails. By having a smaller diameter rod or nail 800 compared to prior art nails of titanium or the like, this would aid in preserving the endosteal/medullary blood supply.

Figure 8:
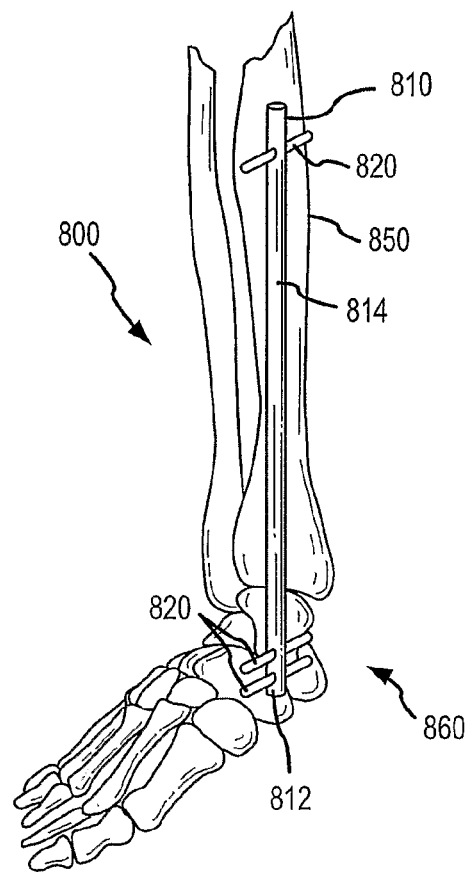
FIG. 8 is an overall view of a bone fixation device according to an alternative embodiment of the present invention.

As shown in FIG. 8, rod or nail 800 is inserted into a bone 850. Rod 800 insertion occurs, in one embodiment, by reaming the bone's medullary canal, and hammering or otherwise driving nail 800 into place. Nail 800 then may be locked relative to the bone with one or more interference or locking screws 820. While the embodiment shown in FIG. 8 depicts a single screw 820 near end 810 and two screws 820 near end 812, it will be appreciated by those skilled in the art that the number of screws 820 may vary within the scope of the present invention. Further, the interference or locking screws 820 may comprise nails, pins or the like. The dimensions of rod 800 and screws 820, including the lengths, widths, diameters, and thicknesses, may vary within the scope of the present invention and may determined, at least in part, by the particular bone(s) and/or joint(s) into which the device is being inserted or otherwise coupled.

In some embodiments, nail or rod 800 is designed to allow for the release of the responsive element or zone portion thereof, allowing the rod or nail 800 to shorten. This is accomplished, at least in part, by having the responsive zone of rod 800 comprise a shape memory alloy such as Nitinol as described above in conjunction with screw 300. In this manner, the release of the responsive element-portion of nail 800 draws locking screws 820 on opposing sides of the responsive zone closer together. Dynamic compression on bone 850 results. In one embodiment, the responsive zone, which may include ends 810, 812 and/or middle section 814, is positioned at a desired location(s) within bone 850 or joint 860 to facilitate bone healing. For example, the responsive zone may be positioned adjacent or spanning a fracture site within bone 850, may be positioned within a joint 860, or at other locations at which increased and/or sustained dynamic pressure is desired.

Bone fixation devices of the present invention, including nails 800, screws 300 and plates 400, may be inserted with one or more sets of instrumentation that also are included within the scope of the present invention. For example, the instrumentation for implantation may be comprised of screws and plates, hammers or other compression devices, clamps or other holding devices, torsion devices such as screwdrivers, torque wrenches or the like for inserting screws, rods and plates. In one embodiment, a torque wrench is provided having a preloaded setting that allows the surgeon to determine whether the screw 300 pseudo elasticity has been activated upon insertion at the fracture site.

Figure 9B:
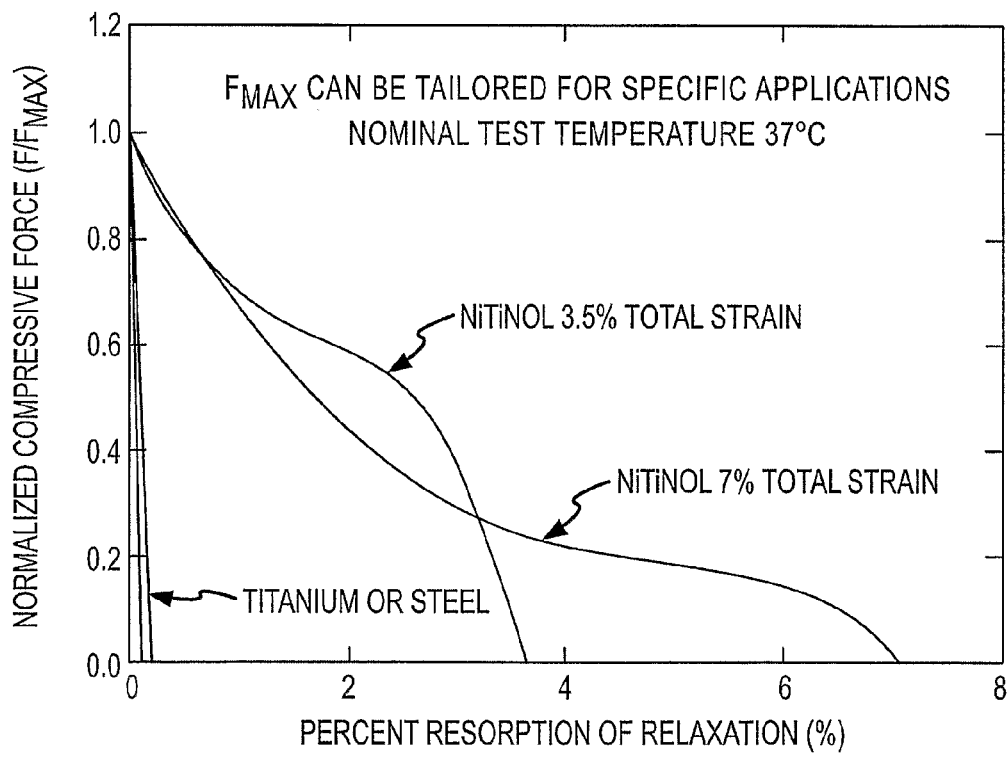

FIG. 9A depicts the stress-strain diagram for living tissues and a nickel titanium alloy. Nickel titanium, and in particular Nitinol, exhibits desirable strain recovery characteristics. The temperature at which Nitinol recovers is known as the transformation temperature ($T_t$). The transformation temperature may be determined using various heat treatments on the material. The material then may demonstrate pseudo elastic (PE) and shape memory (SM) properties, depending at least in part on the relationship between $T_t$ and the surrounding temperature $T_a$ (e.g., atmospheric temperature, internal body temperature, or the like). The PE state is observed when $T_a$ is greater than $T_t$. When the material is stretched from an applied force, a permanent strain is observed. When the force is removed, the material recovers the strain. The SM state occurs when $T_t$ is greater than $T_a$. The material is deformed at above $T_a$, and remains deformed until a temperature is applied which is above $T_t$. These characteristics are useful for fashioning fixation devices according to some embodiments of the present invention. FIG. 9B depicts the inventors experimental results showing the affect of total strain on the unloading profile of SIM Nitinol.

The force that the physician wants to place over fracture site 210 or 610 with screw 100, nail 800, plate 400 or other fixation devices within the scope of the present invention can be defined as $F_R$. The physician also can determine the anticipated change in length ($\Delta L$) of relaxation/resorption needed to maintain the stability in the fracture. This may involve determining the distant or amount the bone and/or surrounding tissues will relax during the healing period. From this information the cross sectional area and length of a bone fixation device, such as screw 100, nail 800 and/or device 400 can be calculated, respectively.

Figure 10A:
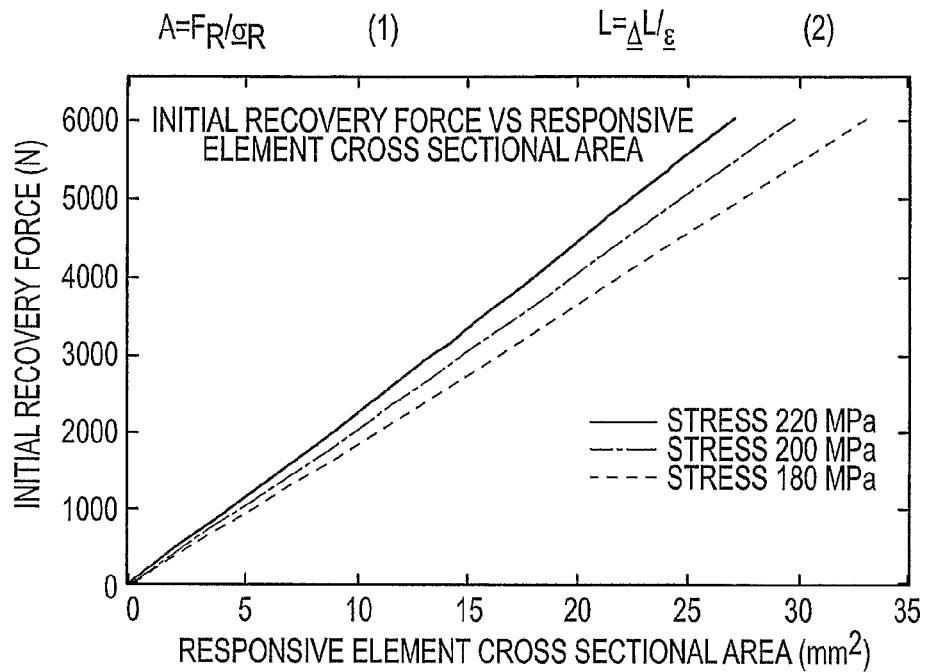
FIGS. 10A and 10B are graphical depictions of characteristics of bone screws and fixation devices according to embodiments of the present invention.
Figure 10B:
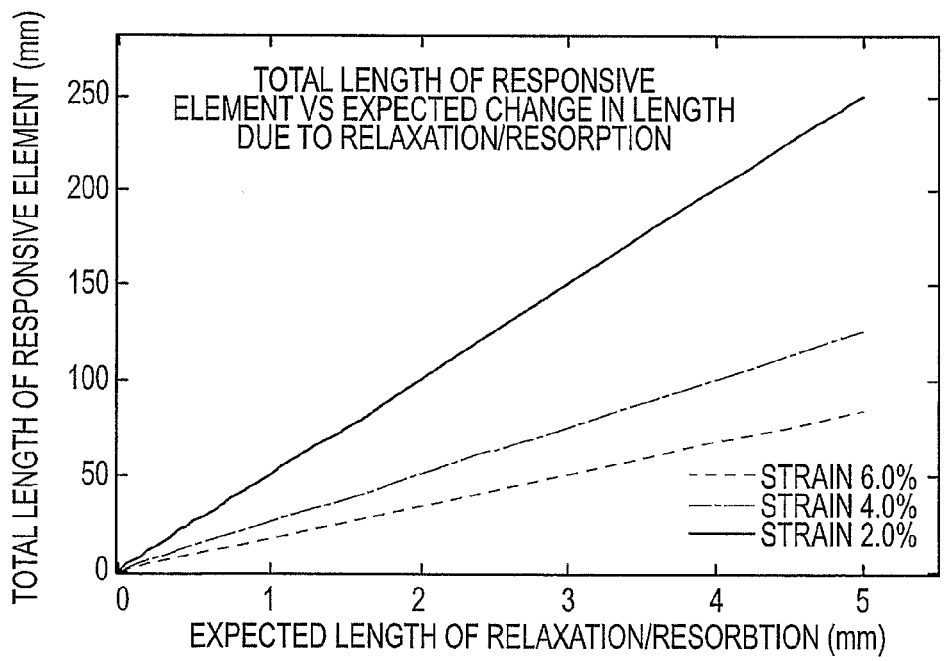

Using equation (1) below, the cross sectional area can be calculated. Using equation (2) below, the total length of the responsive element can be calculated. In these equations, A is the cross-sectional area, $F_R$ is the physician-specified recovery force, $\sigma_R$ is the tensile recovery stress (a material property), L is the length of the responsive zone or element, $\Delta L$ is the physician-specified change in length of the responsive zone or element, and $\epsilon$ is the tensile strain (a material property). The total length and cross sectional area are used for the manufacturing of the plate or screw in order to meet the physician's needs. FIGS. 10A and 10B show an example of possible areas and length, that can be determined by the physician.

$$A = F_R / \sigma_R \qquad (1)$$

$$L = \Delta L / \epsilon \qquad (2)$$

The responsive element or responsive zone, in a preferred embodiment, has a smaller cross sectional area than the non-responsive part. This reduction of the area allows for the stress to be localized over the element or zone, which in turn elongates only the responsive element or zone. By using the responsive element or zone, the application is able to localize the force caused by the Stress Induced Martensite (SIM) over the fracture, while the non-responsive element stays generally strain free and contributes minimal forces to the bone due to SIM.

Several devices and systems of the present invention are developed from a Shape Memory Alloy (SMA) to actively respond to the changes of the human body, especially in the bone response. In some embodiments, the inventors studied and used the SMA nickel titanium, or Nitinol. NiTiNOL is biologically compatible with the endoskeleton structure, as well as being strong and durable. Several embodiments of the present invention harness the material characteristics of NiTiNOL.

The below discussion covers the steps to manufacture a dynamic compression bone screw, nail, bone fixation device or plate, and other active devices from NiTiNOL, and the machining of NiTiNOL devices. A brief description of the heat treating, composition and deformation techniques used will be addressed. It will be appreciated by those skilled in the art that the manufacturing techniques described represent just some of the embodiments of the present invention.

Material Preprocesses

It is desirable to develop an accurate stress strain response for various states of the NiTiNOL. Below are the steps used to characterize a particular composition of an SMA of NiTiNOL according to an embodiment of the present invention:

1. Bars of Hot Rolled Ti-50.9% at % Ni, and Cold Drawn Ti-50.9% at. % Ni. were obtained from Special Metals.
2. The materials are cut into desired bone plate, nail and screw shapes from the bars using Electro Discharge Machining (EDM). This process allowed for the presence of mechanical work to be minimal in the samples. The specimens were cut into dog bone samples for tension and rectangular blocks for compression. All tests are run in monotonic strain control.
3. Various heat treatments were applied to the Hot Rolled Material, based on the use of $Ti_3Ni_4$ precipitants to move the Martensite start ($M_s$) and finish ($M_f$) temperatures, as well as the Austenite start ($A_s$) and finish temperatures ($A_f$). The results were determined through the transformation peaks being observed using a Differential Scanning Calorimeter.
4. The various stress-strain responses were examined with regard to heat treatment. This allows for certain characteristics to be harnessed in the design. The uses of various heat treatments allow for the stress recovery and strain recovery to be changed.
5. Using the material response in its loaded condition, a cross sectional area is designed as briefly discussed in conjunction with FIGS. 10A-10B.

Bone Screw/Nail

Some embodiments of bone fixation devices of the present invention are developed to actively adapt to the resorption across the fracture site. One such bone screw manufacturing process according to the present invention is provided below. The manufacture of other fixation devices within the scope of the present invention follow a similar or same process.

1. Using the manufacturing results 1-5 above, the actual design of the responsive element or responsive zone can be determined. The specific calculations of the responsive element for the bone screw are discussed briefly in conjunction with FIGS. 10A-10B, and in more detail in Provisional Application No. 60/563,952, previously incorporated herein by reference.
2. The bars of NiTiNOL are sent to be EDM into smaller cylindrical sections. At this time, no heat treatment has been applied and the material is said to be in its as-received state.
3. The smaller cylinders are heat treated for about 600° C. for about 30 minutes, which in turn reduces the hardness and places the material in a state more susceptible to machining.
4. The screw is machined, such as on a lathe, at a cutting speed similar to stainless steel (e.g., about 300 RPMs). Concurrently, the NiTiNOL is flooded with cutting fluid to reduce the work hardening effects of the cutting surface.
5. After machining, the final part is heat treated to the appropriate temperature based on the material characterization and design phase, listed above. In a particular embodiment, the heat treatment related to the material composition of 50.9 is about 350° C. for about 1.5 hours.
6. The screw is autoclaved and deployed. The reactive element is stretched using the principle of the screws head and threads.

Bone Fixation Device or Plate

Use of a bone fixation device or a bone plate may be necessary to add a large area of stabilization over the fracture site. The device or plate may be used in unison with a bone screw. The bone fixation device or plate actively adapts to the resorption of a fracture site and compensates for the resorption located at the head and threads of the screws. Below are the instructions used to develop a NiTiNOL bone plate according to an embodiment of the present invention.

1. Using the manufacturing results 1-5, the actual design of the responsive element can be determined. The specifics of the responsive element are discussed briefly in conjunction with FIGS. 10A-10B, and in more detail in Provisional Application No. 60/563,952, previously incorporated herein by reference.
2. Based on the type of fracture and amount of resorption expected, the final compressive force required for the plate to respond to the bone is designed using the stress/strain diagram.
3. The bars of the NiTiNOL are sent to be EDM into the final design of the plates. At this time, no heat treatment has been applied and the material is said to be in its as-received state.
   It is possible to use the above "softening" heat treatment to machine the plates on a mill. The smaller rectangles will be cut from the bar, and then heat treated at about 600° C. for about 30 minutes, which in turn reduces the hardness and places the material in a more "machining friendly" state.
4. The plate has its oxide layer left from the EDM mechanically removed.
5. Based on the results of the material characterization stage, the as-received bone plates are heat treated to get the desired properties. Similar to the screw, the heat treatment related to the material composition of 50.9 is about 350° C. for about 1.5 hours.
6. Once the application of the plate is known, it is stretched using an external device to a predetermined strain and held fixed in place with a brace.
7. The entire setup is then sterilized by autoclave and finally deployed over the fracture site.

Other NiTiNOL Devices Including a Responsive Element

Other devices can benefit from the use of NiTiNOL or other SMA in an active responsive element. For example an interlocking bone marrow nail can be formed. The design of the nail is similar to the screw, and encompasses a similar responsive element. The design comes from the characterization of the NiTiNOL as discussed herein. Still other devices that could incorporate the responsive element include an artificial disk replacement used in a patient's vertebra. The responsive element could be designed to allow different forces between particular vertebrae. For example, a person with a large upper torso has different stress contribution between the upper vertebrae and lower vertebrae, than a person with a smaller torso. Other uses of SMAs such as Nitinol also exist for creating actively responsive elements.

Bone Fixation Systems and Methods of Use and Manufacture

In some embodiments, a bone fixation system can include a bone fixation device having a responsive zone, and a clamp having an end cap and an internal brace. FIGS. 11A and 11B illustrate an end cap 1110 according to one embodiment of the present invention. End cap 1110 includes a first section 1112 and a second section 1114. In some embodiments, an end cap can be designed to couple with or sit at a distal end of an intramedullary nail and provide additional support to a jig. An end cap can also provide a connection for an internal brace. In some cases, an end cap can be manufactured from Ti6Al-4V and can have an internal threaded cavity or other threaded surface. FIG. 12 shows an internal brace 1210 according to one embodiment of the present invention. Internal brace 1210 includes a first section 1212 and a second section 1214. Typically, end cap 1110 and internal brace 1210 are configured for adjustable cooperation. For example, end cap first section 1112 and internal brace first section 1212 can be threadably engaged. In some embodiments, an internal brace can be designed to sit inside an intramedullary nail and provide a barrier or impediment to premature recovery of the nail. An internal brace can be threaded into an end cap, and can be designed to allow for a guide rod to be inserted inside both the brace and the nail construct. In some cases, the internal brace is manufactured from Ti6Al-4V and has an internal threaded cavity or other threaded surface.

FIGS. 13A and 13B show a bone fixation system 1310 according to one embodiment of the present invention. Bone fixation system 1310 includes a bone fixation device 1320 having a responsive zone 1322, and a clamp 1330 having an end cap 1340 and an internal brace 1350. Clamp 1330 is disposed partially within an internal lumen of bone fixation device 1320, where the internal lumen is disposed along an axial length of bone fixation device 1320. Clamp 1330 can be adjusted to a first mode, as shown in FIG. 13A, that induces or maintains a first amount of strain in responsive zone 1322 along the axial length of bone fixation device 1320. Similarly, clamp 1330 can be adjusted to a second mode, as shown in FIG. 13B, that induces or maintains a second amount of strain in responsive zone 1322 along the axial length of bone fixation device 1320. Often, adjustment to or between the first or second mode involves adjusting the length of clamp 1330. In some cases, the amount of strain in the first or second mode can be zero. Clamp 1330 can operate to prevent, inhibit, or otherwise control or modulate recovery in responsive zone 1322. Clamp 1330 may be removably coupled with bone fixation device 1320. It is appreciated that the device may be provided in a packaged state, where the device is held stretched by an end cap and internal brace.

As seen in FIGS. 13A and 13B, end cap first section 1342 is adjustably engaged or coupled with bone fixation device 1320, and end cap second section 1344 is adjustably engaged or coupled with internal brace first section 1352. Relatedly, end cap first section 1342 can be threadably engaged with bone fixation device 1320, and end cap second section 1344 can be threadably engaged with internal brace first section 1352. In some embodiments, a central longitudinal axis 1326 defined by an internal lumen of bone fixation device 1320 can be collinear with a central longitudinal axis 1356 defined by internal brace 1350. In some embodiments, central longitudinal axis 1326 can be collinear with a central longitudinal axis 1346 defined by end cap 1340. Relatedly, central longitudinal axis 1356 can be collinear with central longitudinal axis 1346. It is appreciated that bone fixation device can include any of a variety of osteopathic devices, such as nails, screws, plates, rods, compression rods, vertebral and other fixation devices, and the like.

Responsive zone 1322 can be manufactured or otherwise adapted to have a physical characteristic similar to human tissue, such as bone. For example, the physical characteristic can be a modulus value, for example an elastic modulus value. In some cases, the modulus of the responsive zone can be within a range from about 10 GPa to about 70 GPa. Responsive zone 1322 can include a shape memory material, which may be a shape memory nickel or copper alloy. The shape memory material may include a nickel titanium alloy, a copper zinc aluminum alloy, a copper aluminum nickel alloy, and the like. In some embodiments, responsive zone 1322 is configured to provide a predetermined or preset compressive force across a bone fracture site when the clamp is removed or inactivated. For example, a predetermined or preset compressive force may be within a range from about 2 kN to about 4 kN for AO. It is appreciated that therapeutic loads may lie within, below, or beyond this range. Relatedly, responsive zone 1322 can be configured to recover to a predetermined or preset length, for example when clamp 1330 is removed or inactivated so that it no longer imparts a tension to bone fixation device 1320. In some embodiments, the present invention provides a bone fixation device that includes a machined responsive zone having a hardness value within a range from about 5 HRB to about 60 HRC on the Rockwell B and C Hardness Scales.

The present invention also contemplates method embodiments for preparing bone fixation systems. For example, bone fixation system 1310 can be prepared by providing bone fixation device 1320 having responsive zone 1322, and inserting clamp 1330 at least partially within an internal lumen of bone fixation device 1320. A strain in responsive zone 1322 along the axial length of bone fixation device 1320 can be induced, maintained, or adjusted by setting clamp 1330 to the appropriate configuration. In some embodiments, bone fixation device 1320 is an intramedullary nail manufactured from NiTiNOL using a series of heat treatments to reduce the hardness from the bulk material. After the nail is manufactured an aging treatment can be supplied to the nail to induce a pseudoelastic response at body temperature (e.g. about 37° C.) from the bulk material. The nail can be designed so that during an elongation method only the responsive element will stretch. This can allow for the main recovery of resorption to occur over a bone fracture site. The nail can be designed to recover immediately or quickly upon unloading, thus a clamp or other internal restrain system can be designed to package and maintain the stretched section of the nail.

Figure 15:
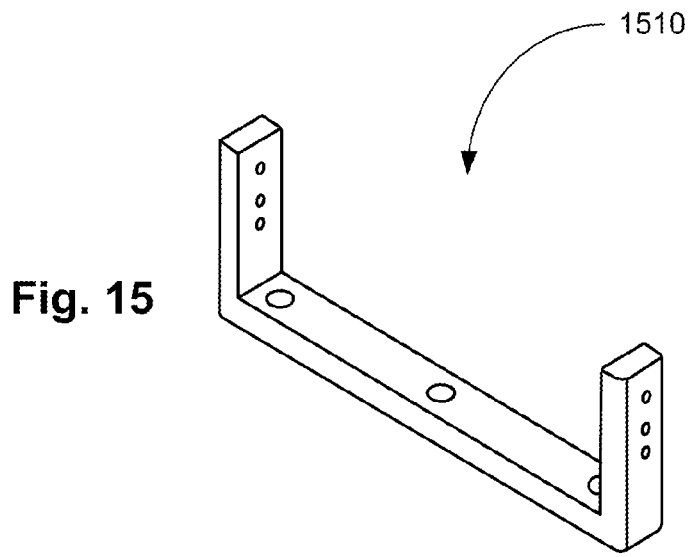
FIG. 15 shows a restrainer bar according to embodiments of the present invention.

FIG. 14 illustrates an external fixation device or jig device 1410 that is designed to maintain the stretched form of a bone fixation device when a clamp is removed therefrom. In some embodiments, a jig can be designed to maintain a stretched form of an intramedullary nail when an internal brace is removed therefrom. An external fixation device or jig can also provide functionality for implantation and locking screw placement. A jig can be preset so that screw holes of the nail, inside the bone, are aligned with screw holes in the jig, outside the leg, thus aiding placement of the locking screws through the soft tissues and bones. FIG. 15 shows a restrainer bar 1510 that can be used to fix an end cap relative to a jig and prevent or inhibit the nail from prematurely traveling up or within the intramedullary cavity. An intramedullary nail, an internal brace, and an end cap can be designed to slip through a restrainer bar until a flange of the end cap comes into contact with the bar. This can lock the intramedullary nail into place and can help align the jig into place. The jig may be configured in any of a variety of suitable shapes. For example, the jig may have a "U" shape.

Figure 16:
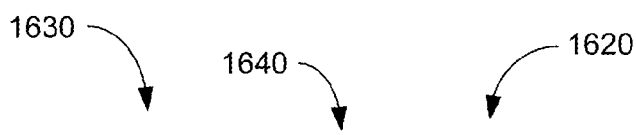
FIG. 16 illustrates a bone fixation device according to embodiments of the present invention.

In some embodiments, the present invention provides a method of deploying a bone fixation device in a patient. The bone fixation device 1610 shown in FIG. 16 is coupled with a clamp 1615 and includes a first portion 1620, a second portion 1630, and a responsive zone 1640 disposed therebetween. In some embodiments, this can represent the stretching and holding of a nail, whereby the nail is held fixed with an internal brace and an end cap. Clamp 1615 is partially disposed within an internal lumen of device 1610, where the internal lumen is disposed along an axial length of device 1610. Claim 1615 can be configured to induce or maintain a strain in responsive zone 1640 along the axial length of device 1610.

Figure 17:
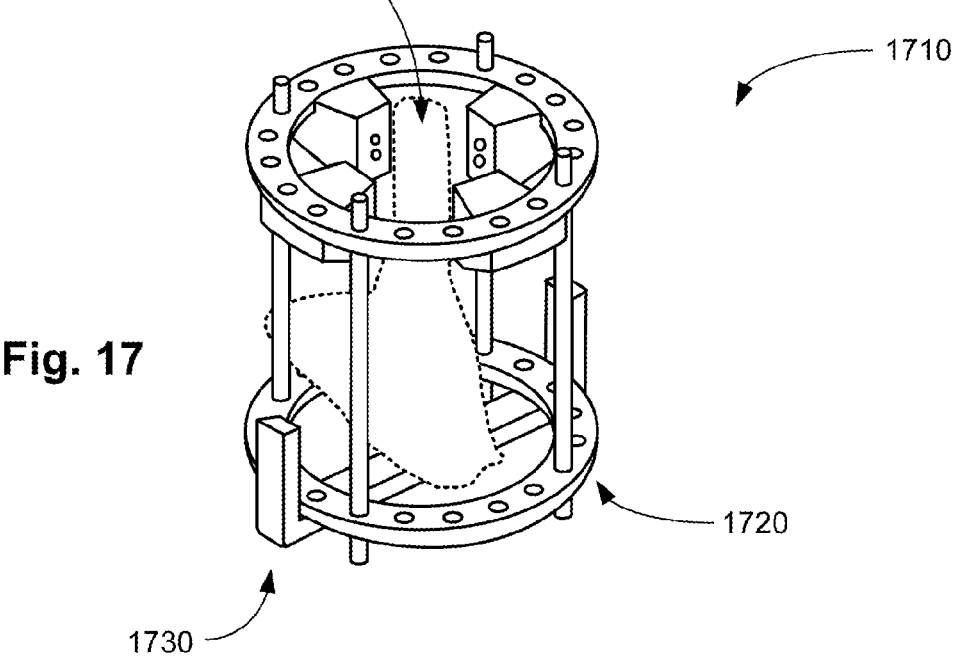
FIG. 17 depicts a patient's leg and a jig and restrainer bar according to embodiments of the present invention.

In an exemplary procedure, a surgeon performs standard techniques to prepare a patient's ankles and subtalar joints for ankle fusion. FIG. 17 depicts an external brace assembly 1710 that includes a jig 1720 and a restrainer bar 1730. Also shown here, relative to external brace assembly 1710, is a patient's lower leg 1740. The external brace assembly can assist the surgeon in properly aligning the ankle for surgery. Using a suitably placed guide wire, a surgeon can ream a hole in the intramedullary cavity to an appropriate size for an outer diameter of an intramedullary nail. In some embodiments, a jig can be placed over a patient's foot or other body part and attach to an intramedullary nail via an end cap at a distal end of the body part, for example at a distal end of the ankle.

Figure 18:
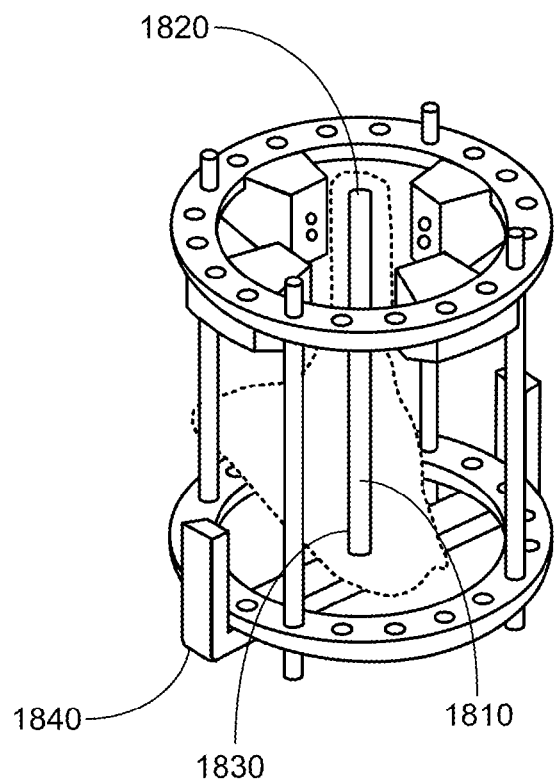
FIG. 18 depicts a patient's leg, a jig and restrainer bar, and a bone fixation device according to embodiments of the present invention.
Figure 19:
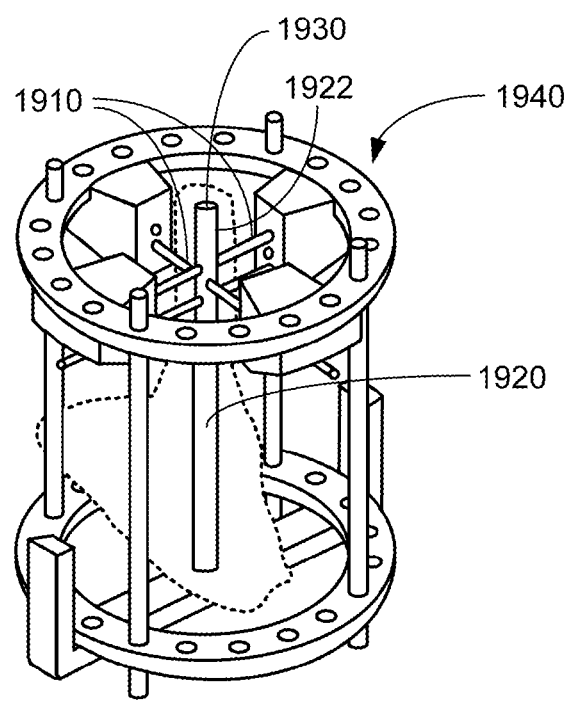
FIG. 19 depicts a patient's leg, a jig and restrainer bar, a bone fixation device, and cross pins according to embodiments of the present invention.
Figure 20:
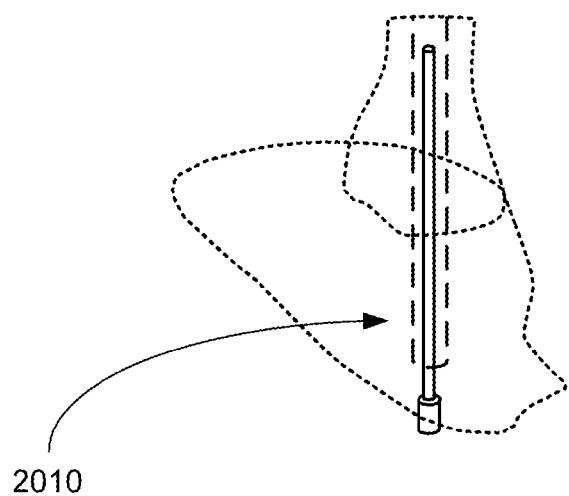
FIG. 20 depicts a patient's leg and a bone fixation device according to embodiments of the present invention.

As shown in FIG. 18, a bone fixation device 1810 can be placed adjacent or inside of a patient's bone 1820, and the first portion 1830 of device 1810 can be coupled with the restrainer bar 1830. In some embodiments, a stretched intramedullary nail construct is inserted into an intermediary cavity until the construct comes into contact with the restrainer bar. When contact is made between the construct and the bar, the restrainer bar can be used to align the nail into the proper position. FIG. 19 shows cross pins 1910 effectively coupling bone fixation device 1920 with a first location 1922 of patient's bone 1930 and stabilizing bone 1930 relative to the jig 1940. Cross pins can also be used to similarly fix a second location of the patient's bone to the bone fixation device and may contain a drill tip. Typically, the bone includes a fracture site disposed between the first and second bone locations. Bone fixation device 1920 can therefore be secured relative to jig 1940. In some embodiments, once an intramedullary nail is embedded and aligned inside of an intermediary canal, the surgeon can drill 2-3 holes to place cross pins across a proximal side of the tibia. The cross pins can be designed to provide a fixation point to transfer a load from an internal brace or nail to a jig. As seen in FIG. 20, once the cross pins are installed, the surgeon can preload the jig by removing the internal brace 2010 using an appropriate device such as a hex Allen key drill or hand tool. As the brace is removed the load is transferred through the intramedullary nail and end cap into the jig. The surgeon can monitor external brace and nail placement.

Figure 21:
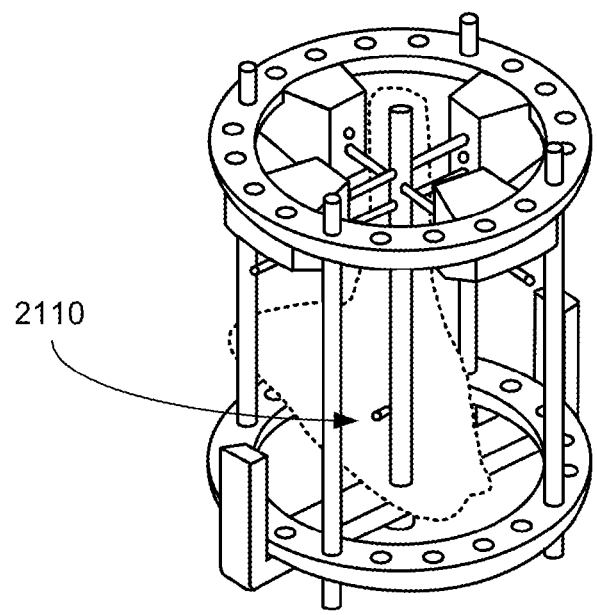
FIG. 21 depicts a patient's leg, a jig and restrainer bar, cross pins, a bone fixation device, and bone screws according to embodiments of the present invention.
Figure 22A:
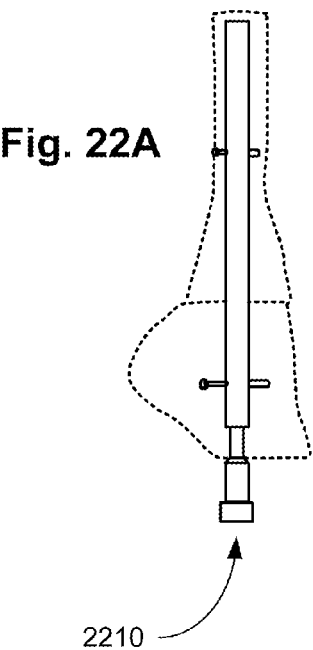
FIGS. 22A and 22B show a patient's leg, a jig and restrainer bar, cross pins, a bone fixation device, and bone screws according to embodiments of the present invention.
Figure 22B:
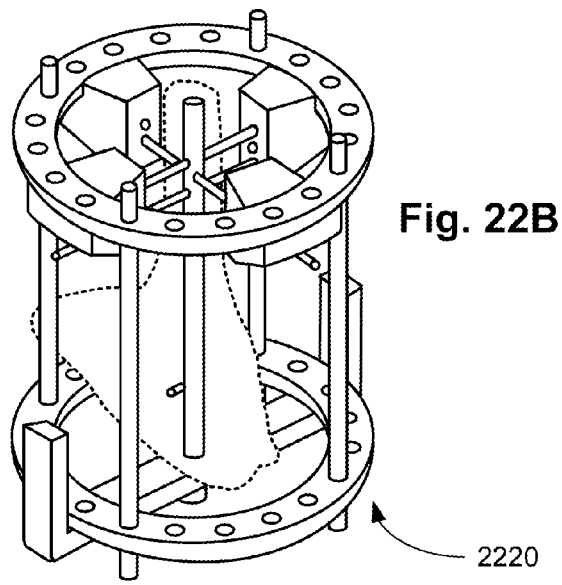
Figure 23:
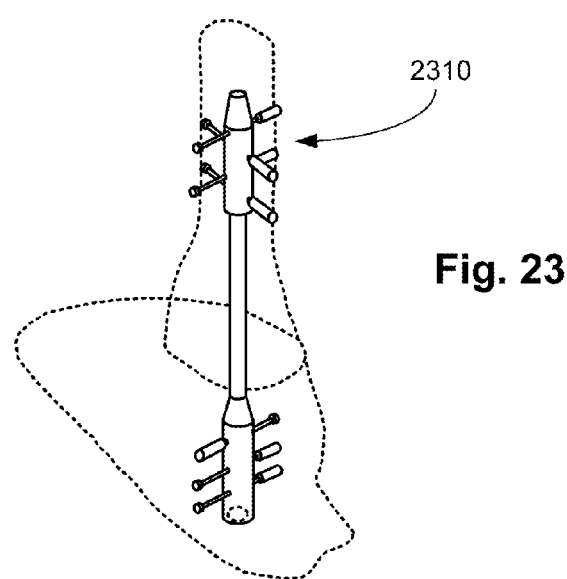
FIG. 23 depicts a patient's leg, a bone fixation device, and bone screws according to embodiments of the present invention.

As illustrated in FIG. 21, after the internal brace has been removed and the load transferred across to the jig, the surgeon can install calcaneal screws 2110 first on the distal side of the ankle and then the proximal/tibial side locking screws can be placed. Bone screws can allow the nail to apply compression through the ankle. As seen in FIGS. 22A and 22B, once the screws have been installed on both ends of the intramedullary nail, the end cap 2210 can be slowly loosened or removed using an appropriate tool, such as an Allan key wrench. The gradual unscrewing of end cap 2210 can transfer the load from the external brace 2220 to the intramedullary nail and ankle. In some embodiments, multiple screws may be installed prior to full end cap removal. As depicted in FIG. 23, after the end cap is fully removed, the cross bars or pins can be removed and replaced with bone screws 2310 to secure the remaining portion of the nail. Once the end cap is removed, the nail is in a dynamic state and applies a constant compressive force across the fusion site. A solid end cap can then be placed in the nail to secure the distal end. The surgeon can then suture the remaining incisions and prepare for post-op. The jig can then be dismantled and removed from the patient's foot. The nail is fully loaded and installed.

The techniques described herein can be used at any part of the body where dynamic axial compressive load is desired. For example, these approaches can be used for treating fractures in long bones fractures, including humeral, radial, tibial, and femoral fractures. Advantageously, these techniques provide for reproducible, true dynamic load, applied from an internal fixation device. Relatedly, these techniques can be used in opposite applications to apply a dynamic distraction force across a site. For example, such opposite applications can be used in limb lengthening procedures or for large "long bone defect implants" for example humeral replacement status post osteosarcoma resection in a non-skeletally mature patient. These systems and methods can also be used to apply controlled distraction/compression in increments activated by radio-frequency or magnetic manipulation. Moreover, the systems and methods can be used to couple a responsive zone with an existing or current implant such as a total hip or a total knee, to allow for greater surgeon margin or error with regard to limb length discrepancies status post joint replacement. In some embodiments, these techniques allow for adjustments months or years after an implant has been placed and the patients individual resorptive bone response has occurred. It is appreciated that these approaches can be implemented in a variety of controllable compression/distention practices involving an internal implant.

Figure 25:
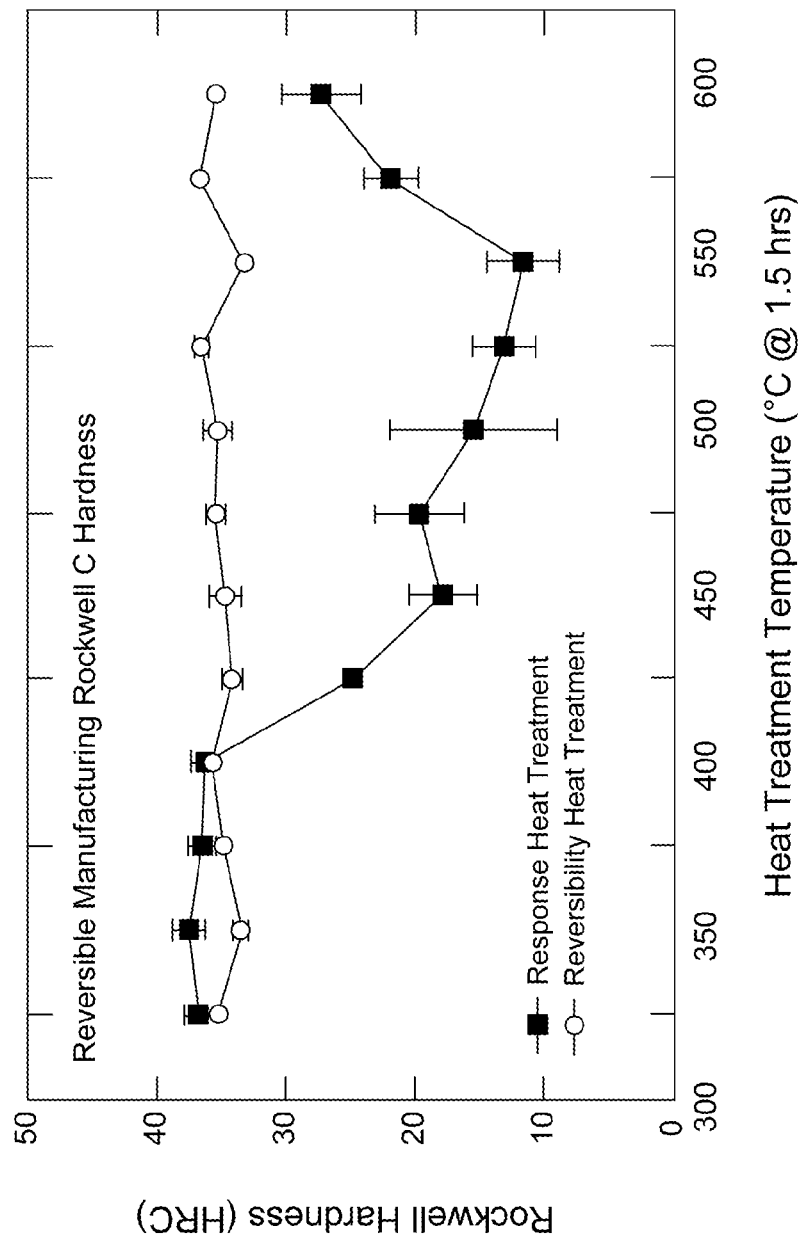
FIG. 25 shows a hardness versus heat treatment graph according to embodiments of the present invention.

FIGS. 24A-24H show a prototypical intramedullary nail with exemplary dimensions. FIG. 25 shows multiple hardness responses achievable from aging of NiTi. Hardness can be related to machinability of a material. In some embodiments, the softer a material is, the easier it is to machine. When a shape memory material such as NiTi behaves pseudoelastically (superelastic) the hardness is at a peak. Thus, the material can be difficult to machine. It may be helpful to age the material into a low hardness state, machine it, then erase the low hardness state and reprogram it to the high hardness state.

In one embodiment, a method of processing a shape material for use in a bone fixation device can include treating the shape memory material with a first treatment to transform the shape memory material from a first state to a second state, machining the shape memory material while it is in the second state, and treating the machined shape memory material with a second treatment to transform the shape memory material from the second state to the third state. Often, the treatments are designed to establish or optimize pseudoelastic or shape memory characteristics in the material. The first treatment may include a first heat cycle of at least 5 minutes, or in some cases of about 5 minutes to about 1.5 hours, at a temperature of about 600° C. or above. It is appreciated that depending on the type of material being processed, the duration and temperature may vary. The first treatment may further include a second heat cycle of at least 5 minutes, or in some embodiments of about 5 minutes to about 1.5 hours, at a temperature of 300° C., 350° C., 400° C., 450° C., 500° C., or 550° C., or at a temperature within a range between about 200° C. to about 550° C. In some embodiments, the first state has a first hardness value, the second state has a second hardness value, and the first hardness value is between about 100% and about 500% of the second hardness value. Relatedly, in some cases the first state has a first shape recovery value, the third state has a third shape recovery value, and the third shape recovery value is at least 95% of the first shape recovery value. The shape memory material can include a shape memory alloy such as a nickel titanium alloy, a copper zinc aluminum alloy, or a copper aluminum nickel alloy, or any precipitated shape memory alloy.

The third state can exhibit an optimal pseudoelastic or superelastic property profile for the shape memory material. Similarly, the third state may also exhibit an optimal shape memory state. In some embodiments, the first state can have a first hardness value, the third state can have a third hardness value, and a difference between the first hardness value and the third hardness value can be less than about 3 HRC on the Rockwell C Hardness Scale. In some cases, this difference may be less than about 10 HRC.

In another embodiment, the present invention provides a method of preparing a bone fixation device. The method includes providing a bone fixation device that includes a shape memory material, and machining the shape memory material while the temperature of the shape memory material is maintained at or above an austenite or r-phase transition temperature. In some embodiments, during the machining the shape memory material remains in a stiff austenite phase and does not transition to a malleable austenite.

Embodiments of the invention have now been described in detail. However, it will be appreciated that the invention may be carried out in ways other than those illustrated in the aforesaid discussion, and that certain changes and modifications may be practiced within the scope of the appended claims. Accordingly, the scope of this invention is not intended to be limited by those specific examples, but rather is to be accorded the scope represented in the following claims.

What is claimed is:

1. A method of manufacturing a shape memory alloy medical device element, the method comprising:
    performing a first heat treatment operation on a shape memory alloy including a first heating cycle of the shape memory alloy to between about 500 degrees Celsius and about 550 degrees Celsius for between about 5 minutes and about 1.5 hours;
    wherein the first heat treatment operation further comprises a second heating cycle performed before the first heating cycle, the second heating cycle comprising heating the shape memory alloy to above about 600 degrees Celsius for between about 5 minutes and about 1.5 hours;
    after the first heat treatment operation, machining the shape memory alloy into the shape memory alloy medical device element; and
    after machining, performing a second heat treatment operation on the shape memory alloy medical device element.

2. The method of claim 1, wherein the first heat treatment operation further comprises:
    transforming the shape memory alloy from a first state to a second state;
    wherein the first state is a hot-rolled state of the shape memory alloy.

3. The method of claim 2, wherein the shape memory alloy in the second state comprises an austenite phase.

4. The method of claim 2, wherein the shape memory alloy has a first hardness value in the first state and the shape memory alloy has a second hardness value in the second state, different from the first hardness value.

5. The method of claim 4, wherein the first hardness value is between about 100 percent and about 500 percent of the second hardness value.

6. The method of claim 2, wherein the second heat treatment operation further comprises:
    transforming the shape memory alloy from the second state to a third state.

7. The method of claim 6, wherein the shape memory alloy in the third state exhibits instability of a martensitic phase of the shape memory alloy at about 37 degrees Celsius.

8. The method of claim 6, wherein the shape memory alloy has a first hardness value in the first state and the shape memory alloy has a third hardness value in the third state, different from the first hardness value.

9. The method of claim 8, wherein the first hardness value and the third hardness value are different by less than about 10 HRC, as measured on the Rockwell C Hardness Scale.

10. The method of claim 9, wherein the first hardness value and the third hardness value are different by less than about 3 HRC, as measured on the Rockwell C Hardness Scale.

11. The method of claim 6, wherein the shape memory alloy has a first shape recovery value in the first state and the shape memory alloy has a second shape recovery value in the third state, different from the first shape recovery value.

12. The method of claim 11, wherein the first shape recovery value is at least 95 percent of the second shape recovery value.

13. The method of claim 1, wherein the first heating cycle of the shape memory alloy is performed below a melting temperature for the shape memory alloy.

14. The method of claim 1, wherein the first heating cycle further comprises:
    heating the shape memory alloy to about 550 degrees for about 1.5 hours.

15. The method of claim 1, wherein the second heat treatment operation further comprises:
    heating the shape memory alloy medical device element to at least about 350 degrees Celsius for about 1.5 hours.

16. The method of claim 1, wherein the second heat treatment operation further comprises:
    heating the shape memory alloy medical device element to about 350 degrees Celsius for about 1.5 hours.

17. The method of claim 1, wherein the second heat treatment operation further comprises:
    heating the shape memory alloy medical device element to about 400 degrees Celsius for about 1.5 hours.

18. The method of claim 1, wherein machining further comprises:
    cutting the shape memory alloy on a lathe at a cutting speed of about 300 revolutions per minute.

19. The method of claim 1, further comprising:
    deforming the shape memory alloy medical device element.

20. The method of claim 19, wherein the deforming further comprises:
    creating a martensitic phase in at least part of the shape memory alloy medical device element.

21. The method of claim 19, wherein the deforming is performed after the second heat treatment operation is performed.

22. The method of claim 19, wherein the deforming is performed while the shape memory alloy medical device element is inside a patient.

23. The method of claim 22, further comprising:
    primarily fixing the shape memory alloy medical device element to a first bone element of the patient.

24. The method of claim 23, wherein the primarily fixing is performed before the deforming is performed.

25. The method of claim 24, further comprising:
    secondarily fixing the shape memory alloy medical device element to a second bone element of the patient.

26. The method of claim 25, wherein the secondarily fixing is performed after the primarily fixing is performed.

27. The method of claim 1, further comprising:
    removing an oxide layer from shape memory alloy.

28. The method of claim 27, wherein removing is performed mechanically.

29. The method of claim 27, wherein removing is performed after performing the first heat treatment operation on the shape memory alloy.

* * * * *